(12) United States Patent
Diesendruck et al.

(10) Patent No.: US 11,883,813 B2
(45) Date of Patent: Jan. 30, 2024

(54) CARBAZOLIUM SALT AND USE THEREOF IN ANION EXCHANGE MEMBRANES

(71) Applicant: Technion Research & Development Foundation Limited, Haifa (IL)

(72) Inventors: Charles Eliezer Diesendruck, Binyamina-Giv'at Ada (IL); Dario Dekel, Kiryat-Bialik (IL)

(73) Assignee: Technion Research & Development Foundation Limited, Haifa (IL)

( * ) Notice: Subject to any disclaimer, the term of this patent is extended or adjusted under 35 U.S.C. 154(b) by 186 days.

(21) Appl. No.: 17/271,775

(22) PCT Filed: Aug. 29, 2019

(86) PCT No.: PCT/IL2019/050975
§ 371 (c)(1),
(2) Date: Feb. 26, 2021

(87) PCT Pub. No.: WO2020/044348
PCT Pub. Date: Mar. 5, 2020

(65) Prior Publication Data
US 2021/0322968 A1      Oct. 21, 2021

Related U.S. Application Data

(60) Provisional application No. 62/724,710, filed on Aug. 30, 2018.

(51) Int. Cl.
*B01J 41/13* (2017.01)
*B01J 41/14* (2006.01)
*B01J 47/12* (2017.01)

(52) U.S. Cl.
CPC ............... *B01J 41/13* (2017.01); *B01J 41/14* (2013.01); *B01J 47/12* (2013.01)

(58) Field of Classification Search
CPC ............. B01J 41/13; B01J 41/14; B01J 47/12
(Continued)

(56) References Cited

U.S. PATENT DOCUMENTS

| 4,699,863 | A | | 10/1987 | Sawatari et al. |
| 5,501,724 | A | * | 3/1996 | Loff .................. C09D 5/32 |
| | | | | 106/11 |

(Continued)

FOREIGN PATENT DOCUMENTS

| DE | 3542701 | 6/1986 |
| JP | 61284487 | 12/1986 |

(Continued)

OTHER PUBLICATIONS

S. Aharonovich et al. "An Effective Synthesis of N.N.-Diphenyl Carbozolium Salts", Synlett, 29(10), 2018, pp. 1314-1318 (Year: 2018).*
International Preliminary Report on Patentability dated Mar. 2, 2021 From the International Bureau of WIPO Re. Application No. PCT/IL2019/050975. (8 Pages).
International Search Report and the Written Opinion dated Dec. 11, 2019 From the International Searching Authority Re. Application No. PCT/IL2019/050975. (14 Pages).

(Continued)

*Primary Examiner* — Michael M. Bernshteyn

(57) ABSTRACT

Compositions comprising a tetraaryl ammonium salt, a tetraaryl ammonium salt covalently bound to a polymer and methods for manufacturing the same are disclosed. The disclosed compositions are useful e.g., for an anion exchange membrane, or an anion conducting polymer, and may further be used in electrochemical devices such as alkaline fuel cells, and alkaline redox-flow batteries.

18 Claims, 10 Drawing Sheets

(58) Field of Classification Search
USPC .......................................................... 521/27
See application file for complete search history.

(56) References Cited

U.S. PATENT DOCUMENTS

| | | | | |
|---|---|---|---|---|
| 5,607,567 | A | * | 3/1997 | Yun .................... G01N 27/3335 204/403.08 |
| 2012/0207677 | A1 | * | 8/2012 | Elmaleh ............. C07D 295/073 424/1.89 |
| 2015/0171335 | A1 | * | 6/2015 | Kim ................... H10K 85/6572 257/40 |

FOREIGN PATENT DOCUMENTS

| | | |
|---|---|---|
| JP | 4-349462 | 12/1992 |
| WO | WO 01/88520 | 11/2001 |
| WO | WO 2017/107117 | 6/2017 |
| WO | WO-2017107117 A1 * | 6/2017 ............ C08F 112/32 |
| WO | WO 2020/044348 | 3/2020 |

OTHER PUBLICATIONS

Aharonovich et al. "An Effective Synthesis of N,N-Diphenyl Carbazolium Salts", Synlett 29(10):1314-1318, 2018.

Hellwinkel et al. "Ringschlussreaktionen yon 2'-Heterosubstituierten Biphenyl2-diazonium-Salzen zu (Spiro)Cyclischen TetraarylammoniumSalzen und Tribenz[b.d.f]azcpinen)", Chemische Berichte, 105(3): 880-906, Mar. 1972. (with English Abstract).

Nefedov et al. "Comparative Study of Ion-Molecular Reactions of Tritiated Phenyl-Cations with Organic Nitrogen and Phosphorus Derivatives; Sravnitel'Noe Issledovanie Ion-Molekulyarnykh Reakstij tritirovannykh fenil-kationov s orghanicheskimi proizvodnymi azota i fosfora", Radiokhimiya; Journal,36(4):357-361, Dec. 31, 1994. Abstract.

Nesmeyanov et al. "Nitration of bis-2, 2'-Diphenyleneammonium Cation", Bulletin of the Academy of Sciences of the USSR, Division of Chemical Science, 22: 2575-2578, 1973.

* cited by examiner

CARBAZOLIUM SALT AND USE THEREOF IN ANION EXCHANGE MEMBRANES

CROSS REFERENCE TO RELATED APPLICATIONS

This application is a National Phase of PCT Patent Application No. PCT/IL2019/050975 having International filing date of Aug. 29, 2019, which claims the benefit of priority from U.S. Provisional Patent Application No. 62/724,710, filed on Aug. 30, 2018, entitled "USE OF CARBAZOLIUM SALTS IN ANION-EXCHANGE MEMBRANES", the contents of which are incorporated by reference herein in their entirety.

FIELD OF THE INVENTION

The invention relates inter alia to compositions comprising quaternary aryl ammonium salts, articles comprising the same and methods for preparation thereof.

BACKGROUND

Anion-exchange membranes with long lifetimes are key parts in electrochemical devices, such as alkaline fuel cells, alkaline water electrolyzers, alkaline redox-flow batteries, metal-air batteries, among others. Several materials have been previously developed, and yet, few membranes show long-term performance upon activation of the device.

Anion-exchange membranes possess cationic groups either as pendent sidechains or as part of the main chain. Independently of their positioning, these organic cations are prone to nucleophilic and/or base attack by hydroxide ions, which neutralize the cations and extinguish their anion-exchange and anion conducting capacity. Given that typical degradation mechanisms are SN2 type or E2 type, the use of tetraaryl ammonium salts can inhibit these pathways, leading to more kinetically stable cations which may decompose via alternative mechanisms such as SNAr and benzyne.

Known synthetic routes to tetraaryl ammonium salts are tedious, requiring numerous synthetic steps, thus being inefficient and expensive. Therefore, there is a need for optimization of the known synthetic procedures, allowing an efficient synthesis of tetraaryl ammonium salts and numerous conjugates comprising the same.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

In one aspect of the invention, there is a composition comprising a tetraaryl ammonium salt represented by Formula I:

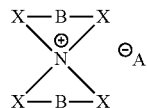

wherein:
each X independently comprises an aryl ring;
each B represents independently a bond, or is absent;
and A- is a counter anion, and if at least one B is a bond then at least one X is selected from the group consisting of: a substituted aryl ring, a heteroaryl ring, a substituted heteroaryl ring or any combination thereof.

In one embodiment, the tetraaryl ammonium salt is represented by Formula II:

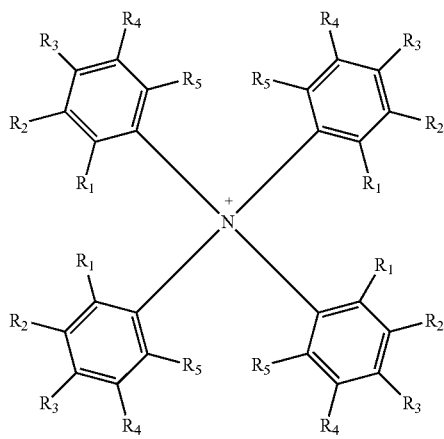

wherein R1, R2, R3, R4 and R5 are each independently selected from the group consisting of: hydrogen, an alkyl group, an alkoxy group, a halo group, a perfluoroalkyl group, a perfluoroalkoxy group, a heteroalkyl group, an aryl group, a hydroxy group, an amino group, an aminoalkyl group, a guanidine group, a thioalkoxy group, a mercapto group, a cyano group, a haloalkyl group, an arylalkyl group, a nitro group, an azo group, a sulfonate group, a sulfinyl group, a vinyl group, an allyl group, an alkyne, a thioalkyl group, an alkylhydroxy group, a keto group, a carboxylic acid derivative, and a sulfone group or any combination thereof, and A- is a counter anion.

In one embodiment, the tetraaryl ammonium salt is represented by Formula III:

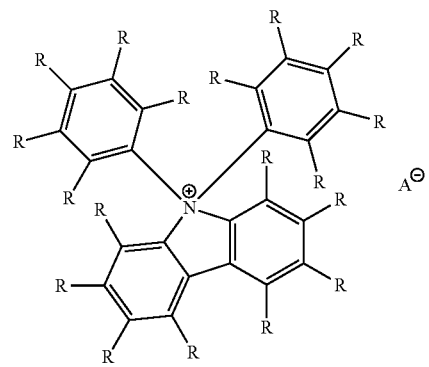

wherein each R represents a substituent independently selected from the group consisting of: a halo group, an alkoxy group, a perfluoroalkyl group, a perfluoroalkoxy group, a heteroalkyl group, an aryl group, a hydroxy group, a mercapto group, an amino group, an aminoalkyl group, a guanidine group, a thioalkoxy group, a cyano group, a haloalkyl group, an arylalkyl group, a nitro group, an azo group, a sulfonate group, a sulfinyl group, a vinyl group, an allyl group, an alkyne, a thioalkyl group, an alkylhydroxy group, a keto group, a carboxylic acid derivative, and a sulfone group or is absent, and A- is a counter anion; and wherein said tetraaryl ammonium comprises at least one substituent.

In one embodiment, the tetraaryl ammonium salt is represented by Formula IV:

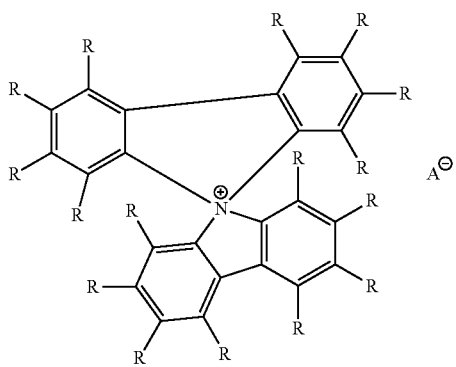

wherein each R represents a substituent independently selected from the group consisting of: a halo group, an alkoxy group, a perfluoroalkyl group, a perfluoroalkoxy group, a heteroalkyl group, an aryl group, a hydroxy group, a mercapto group, an amino group, an aminoalkyl group, a guanidine group, a thioalkoxy group, a cyano group, a haloalkyl group, an arylalkyl group, a nitro group, an azo group, a sulfonate group, a sulfinyl group, a vinyl group, an allyl group, an alkyne, a thioalkyl group, an alkylhydroxy group, a keto group, a carboxylic acid derivative, and a sulfone group or any combination thereof, and A- is a counter anion; and wherein said tetraaryl ammonium comprises at least one substituent.

In another aspect of the invention, there is a composition comprising a tetraaryl ammonium salt covalently bound to a polymer.

In one embodiment, the tetraaryl ammonium salt is represented by Formula I:

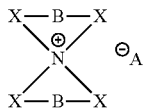

wherein:
each X independently comprises an aryl ring;
each B represents independently a bond, or is absent; and
A⁻ is a counter anion.

In one embodiment, the tetraaryl ammonium salt is covalently bound to a polymer backbone, to a polymer sidechain, or both.

In one embodiment, the polymer comprises any one of: polycarbonate, polyurea, polyurethane, vinyl polymers, polyalkyl, polybutadiene, polyamide, PEG, polypropylene glycol, poly(tetrahydrofuran), polyacrylonitrile (PAN), polyisobutene, polyisoprene, polychloroprene, polystyrene (PS), polystyrene-coisoprene, poly(vinyl chloride) (PVC), polyethylene, polypropylene, polytetrafluoroethylene (PTFE), polyvinyl cyclohexane, poly(vinyl acetate) (PVA), methylated cellulose, polyvinylidene difluoride (PVDF), polyphenylene oxide (PPE), polysulfone or any combination thereof.

In one embodiment, a molar ratio of the polymer to the tetraaryl ammonium salt within said composition is in a range from 1:0.1 to 1:5.

In one embodiment, the composition substantially maintains its chemical identity at a pH ranging from 1 to 14.

In another aspect of the invention there is a method for synthesizing the tetraaryl ammonium salt of the invention, comprising the steps of:
 a. providing a biaryl compound comprising (i) a diazonium salt; (ii) a triaryl amine, wherein said (i) and (ii) are in a position suitable for intramolecular cyclization;
 b. performing an intramolecular cyclization under suitable conditions, thereby obtaining the tetraaryl ammonium salt.

In one embodiment, the method further comprises the steps of:
 a. providing a diaminobiaryl compound;
 b. arylating at least one amino group of the diaminobiaryl compound to obtain a triaryl amine;
 c. diazotizing a free amino group by reacting the triaryl amine with a diazotation compound, to obtain a diazonium salt, thereby obtaining the biaryl compound comprising the diazonium salt and the triaryl amine.

In one embodiment, the position suitable for intramolecular cyclization is a 2,2' position.

In one embodiment, arylating comprises reacting the diaminobiaryl compound with an aryl comprising a leaving group, optionally in the presence of a metal-based catalyst.

In one embodiment, the leaving group comprises any one of: a halo group, a nitro group, an azo group, a quaternary amino group.

In one embodiment, the metal-based catalyst is a Cu(I) based catalyst, further comprising a bidentate ligand.

In one embodiment, a molar ratio of the diaminobiaryl compound to the metal-based catalyst is at least 1:0.01.

In one embodiment, a molar ratio of the diaminobiaryl compound to the aryl comprising the leaving group is at least 1:1.

In one embodiment, the diazotation compound comprises a source of nitroso compound (N≡O+).

In one embodiment, the suitable conditions comprise a temperature in a range selected from 20 to 100° C.

In one embodiment, the suitable conditions further comprise adding a base.

In one embodiment, providing further comprises mixing the diaminobiaryl compound or the biaryl compound with a solvent, thereby forming a solution.

In one embodiment, the diaminobiaryl compound is at a molar concentration ranging from 0.01 to 3 mol/L within the solution.

In another aspect of the invention, there is an article comprising the composition of the invention.

In one embodiment, the article is for use as an anion exchange membrane, an anion exchange ionomer, and an anion conducting polymer.

In one embodiment, the article is in a form of an alkaline fuel cell, an alkaline water electrolyzer, an alkaline redox-flow battery, a metal-air battery, or a capacitor.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1A:
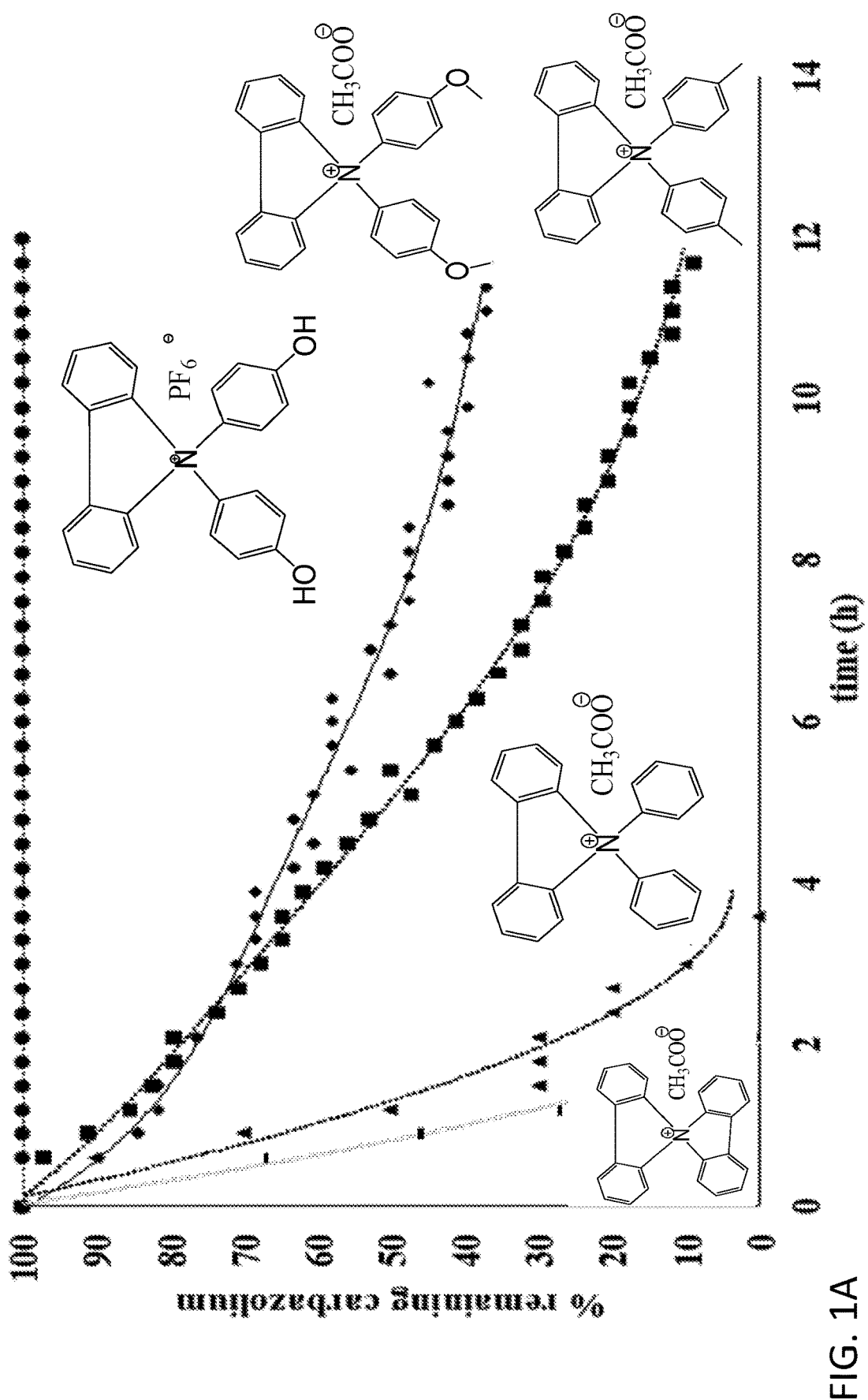
FIG. 1A is a graph showing a decomposition of different carbazoliums using 0.5 mol/L hydroxide in dry DMSO-d6. Hydration level of hydroxide is 4 water molecules/hydroxide, test carried out at room temperature.

The present invention, in one aspect thereof, is directed to a composition comprising a substituted tetraaryl ammonium salt. In some embodiments, the present invention is directed to a composition comprising a tetraaryl ammonium salt covalently bound to a polymer. In another aspect, the present invention is directed to a method of synthesizing a tetraaryl ammonium salt, wherein the tetraaryl ammonium salt is optionally bound to a polymer.

The present invention is based in part on a surprising finding, that N,N-(4-hydroxyphenyl)-carbazolium salt exhibited a superior chemical stability under alkaline conditions, as compared to another tetraaryl ammonium salts and to ammonium salts comprising aliphatic substituents.

Tetraaryl Ammonium Salts

In one aspect of the invention, there is a composition comprising a tetraaryl ammonium salt being represented by Formula 1:

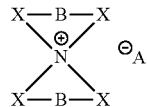

wherein:
each X independently comprises an aryl ring;
each B represents independently a bond, or is absent;
and A- is a counter anion, and if at least one B is a bond then at least one X is selected from the group consisting of: a substituted aryl ring, a heteroaryl ring, a substituted heteroaryl ring or any combination thereof.

In some embodiments, a substituted aryl ring comprises one or more substituents selected from the group consisting of: a hydroxy group, an alkoxy group, an amino group, an aminoalkyl group, a guanidine group, a thioalkoxy group, a mercapto group, a cyano group, a haloalkyl group, an arylalkyl group, a nitro group, an azo group, a heteroalkyl, a sulfonate group, a sulfinyl group, a vinyl group, an allyl group, an alkyne, a thioalkyl group, an alkylhydroxy group, a keto group, a carboxylic acid derivative, and a sulfone group or any combination thereof.

In some embodiments, the one or more substituents are selected from the group consisting of: a hydroxy group, an alkoxy group, an amino group, an aminoalkyl group, a mercapto group, a cyano group, an azo group, a vinyl group, an allyl group, an alkyne, a thioalkyl group, an alkylhydroxy group, and a carboxylic acid derivative, or any combination thereof.

In some embodiments, the one or more substituents are selected from the group consisting of: a hydroxy group, an alkoxy group, an amino group, an aminoalkyl group, a mercapto group, an azo group, a vinyl group, an allyl group, an alkyne, a thioalkyl group, and an alkylhydroxy group or any combination thereof.

In some embodiments, the one or more substituents are selected from the group consisting of: a hydroxy group, an alkoxy group, an amino group, an aminoalkyl group, and an alkylhydroxy group or any combination thereof.

Non-limiting examples of counter anions include but are not limited to: chloride, bromide, fluoride, hydroxide, acetate, and hexafluorophosphate ($PF_6^-$) or a combination thereof.

In some embodiments, the substituted aryl ring comprises an aromatic ring. In some embodiments, the substituted aryl ring comprises one or more aromatic rings. In some embodiments, the substituted aryl ring comprises one or more bicyclic aromatic rings.

In some embodiments, the tetraaryl ammonium salt comprises a quaternary amine covalently bound to one or more bicyclic aromatic rings. In some embodiments, the tetraaryl ammonium salt comprises a quaternary amine covalently bound to two or more bicyclic aromatic rings.

Non-limiting examples of bicyclic aromatic rings include but are not limited to: a fused aromatic ring, bridged aromatic ring, and a spirocyclic aromatic ring or a combination thereof.

In some embodiments, the tetraaryl ammonium salt comprises a quaternary amine covalently bound to one or more biaryl compound. In some embodiments, the tetraaryl ammonium salt comprises a quaternary amine covalently bound to two or more biaryl compounds.

Non-limiting examples of biaryl compounds include but are not limited to: biphenyl, binaphtyl, bipyridine, terphenyl, terpyridine and a combination or a derivative thereof.

In some embodiments, the tetraaryl ammonium salt is represented by Formula 2:

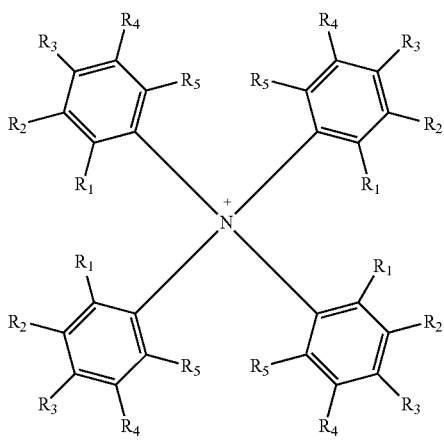

wherein $R_1$, $R_2$, $R_3$, $R_4$ and $R_5$ are each independently selected from the group consisting of: hydrogen, an alkyl group, an alkoxy group, a halo group, a perfluoroalkyl group, a perfluoroalkoxy group, a heteroalkyl group, an aryl group, a hydroxy group, an amino group, an aminoalkyl group, a guanidine group, a thioalkoxy group, a mercapto group, a cyano group, a haloalkyl group, an arylalkyl group, a nitro group, an azo group, a sulfonate group, a sulfinyl group, a vinyl group, an allyl group, an alkyne, a thioalkyl group, an alkylhydroxy group, a keto group, a carboxylic acid derivative, and a sulfone group or any combination thereof; and $A^-$ is a counter anion.

In some embodiments, $R_1$, $R_2$, $R_3$, $R_4$ and $R_5$ are each independently selected from the group consisting of: hydrogen, an alkyl group, a hydroxy group, a halo group, an alkoxy group, an amino group, an aminoalkyl group, a guanidine group, a thioalkoxy group, a mercapto group, a cyano group, a haloalkyl group, an arylalkyl group, a nitro group, an azo group, a sulfonate group, a sulfinyl group, a vinyl group, an allyl group, an alkyne, a thioalkyl group, an alkylhydroxy group, a keto group, a carboxylic acid derivative, and a sulfone group or any combination thereof.

In some embodiments, $R_1$, $R_2$, $R_3$, $R_4$ and $R_5$ are each independently selected from the group consisting of: hydrogen, an alkyl group, a hydroxy group, a halo group, an alkoxy group, an amino group, an aminoalkyl group, a mercapto group, an azo group, a vinyl group, an allyl group, an alkyne, a thioalkyl group, and an alkylhydroxy group or any combination thereof.

In some embodiments, $R_1$, $R_2$, $R_3$, $R_4$ and $R_5$ are each independently selected from the group consisting of: hydrogen, an alkyl group, a hydroxy group, an alkoxy group, an amino group, an aminoalkyl group, a halo group, and an alkylhydroxy group or any combination thereof.

In some embodiments, the tetraaryl ammonium salt is represented by Formula 3:

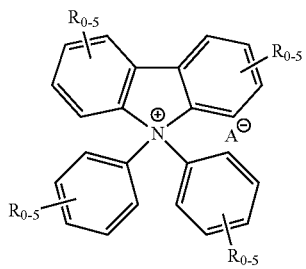

wherein $R_{0-5}$ represents 0 to 5 substituents, wherein at least one substituent is independently selected from the group consisting of: a halo group, an alkoxy group, a perfluoroalkyl group, a perfluoroalkoxy group, a heteroalkyl group, an aryl group, a hydroxy group, a mercapto group, an amino group, an aminoalkyl group, a guanidine group, a thioalkoxy group, a cyano group, a haloalkyl group, an arylalkyl group, a nitro group, an azo group, a sulfonate group, a sulfinyl group, a vinyl group, an allyl group, an alkyne, a thioalkyl group, an alkylhydroxy group, a keto group, a carboxylic acid derivative, and a sulfone group or any combination thereof, and $A^-$ is a counter anion; and wherein the tetraaryl ammonium comprises at least one substituent.

In some embodiments, at least one substituent is independently selected from the group consisting of: a halo group, a hydroxy group, an alkoxy group, an amino group, an aminoalkyl group, a guanidine group, a thioalkoxy group, a mercapto group, a cyano group, a haloalkyl group, an arylalkyl group, a nitro group, an azo group, a sulfonate group, a sulfinyl group, a vinyl group, an allyl group, an alkyne, a thioalkyl group, an alkylhydroxy group, a keto group, a carboxylic acid derivative, and a sulfone group or any combination thereof.

In some embodiments, at least one substituent is independently selected from the group consisting of: hydrogen, a hydroxy group, an alkoxy group, an amino group, an aminoalkyl group, a mercapto group, an azo group, a vinyl group, an allyl group, an alkyne, a thioalkyl group, and an alkylhydroxy group or any combination thereof.

In some embodiments, at least one substituent is independently selected from the group consisting of: hydrogen, a hydroxy group, a halo group, an alkoxy group, an amino group, an aminoalkyl group, and an alkylhydroxy group or any combination thereof.

In some embodiments, at least one substituent is independently selected from the group consisting of: hydrogen, a hydroxy group, and an alkoxy group or any combination thereof.

In some embodiments, the tetraaryl ammonium salt is represented by any of Formulae 3a-3c:

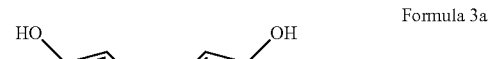

Formula 3a

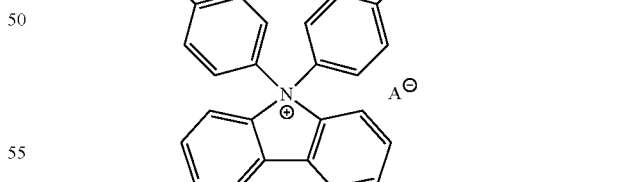

Formula 3b

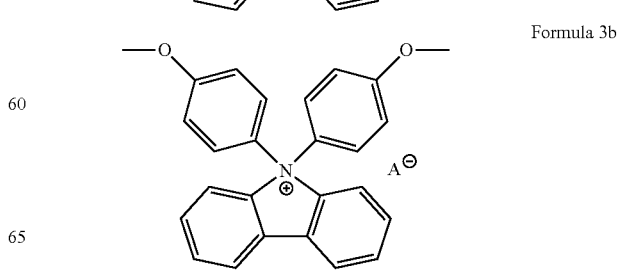

-continued

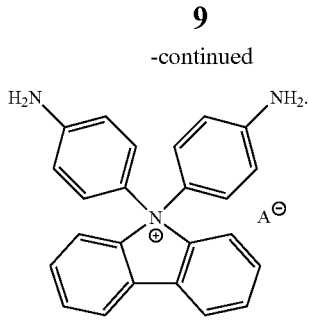

Formula 3c

In some embodiments, the tetraaryl ammonium salt is represented by Formula 4:

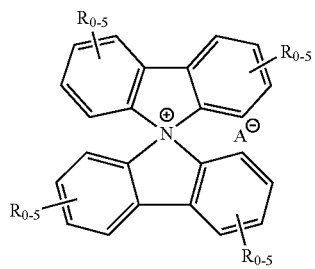

wherein $R_{0-5}$ and $A^-$ are as described hereinabove.

Polymer—Tetraaryl Ammonium Salt Conjugates

In another aspect of the invention, there is a composition comprising a tetraaryl ammonium salt covalently bound to a polymer.

In some embodiments, the tetraaryl ammonium salt covalently bound to a polymer is represented by Formula 5:

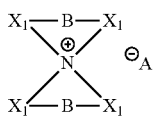

wherein each $X_1$ independently comprises an alkyl, a substituted alkyl, an aryl ring, a substituted aryl ring, a heteroaryl ring, a substituted heteroaryl ring or any combination thereof, and wherein B and $A^-$ are as described hereinabove.

In some embodiments, the tetraaryl ammonium salt covalently bound to a polymer is represented by any one of Formulae 6-8:

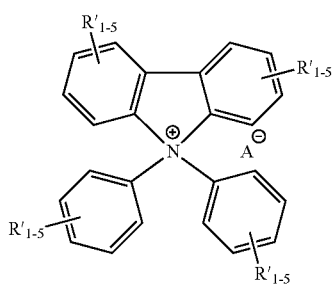

Formula 6

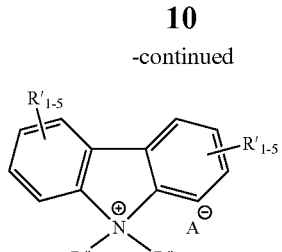

Formula 7

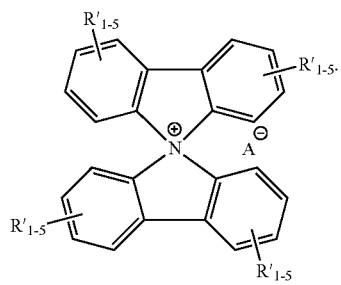

Formula 8

In some embodiments, the tetraaryl ammonium salt covalently bound to a polymer is represented by Formula 2.

In some embodiments, each $R'_{1-5}$ represents 1 to 5 substituents independently selected from the group consisting of: hydrogen, a halo group, an alkoxy group, a perfluoroalkyl group, a perfluoroalkoxy group, a heteroalkyl group, an aryl group, a hydroxy group, a mercapto group, an amino group, an aminoalkyl group, a guanidine group, a thioalkoxy group, a cyano group, a haloalkyl group, an arylalkyl group, a nitro group, an azo group, a sulfonate group, a sulfinyl group, a vinyl group, an allyl group, an alkyne, a thioalkyl group, an alkylhydroxy group, a keto group, a carboxylic acid derivative, and a sulfone group or any combination thereof, and $A^-$ is a counter anion.

In some embodiments, each $R'_{1-5}$ represents 1 to 5 substituents independently selected from the group consisting of: hydrogen, a halo group, an alkoxy group, a perfluoroalkyl group, a perfluoroalkoxy group, a heteroalkyl group, an aryl group, a hydroxy group, a mercapto group, an amino group, an aminoalkyl group, a guanidine group, a thioalkoxy group, a cyano group, a haloalkyl group, an arylalkyl group, a nitro group, an azo group, a vinyl group, an allyl group, an alkyne, a thioalkyl group, an alkylhydroxy group, or any combination thereof.

In some embodiments, each $R'_{1-5}$ represents 1 to 5 substituents independently selected from the group consisting of: hydrogen, a halo group, an alkoxy group, a perfluoroalkyl group, a perfluoroalkoxy group, a heteroalkyl group, an aryl group, a hydroxy group, an amino group, an aminoalkyl group, a mercapto group, a vinyl group, an allyl group, an alkyne, a thioalkyl group, an alkylhydroxy group, or any combination thereof.

In some embodiments, each $R'_{1-5}$ represents 1 to 5 substituents independently selected from the group consisting of: hydrogen, a halo group, an alkoxy group, a hydroxy group, a mercapto group, an amino group, an aminoalkyl group, a vinyl group, an allyl group, an alkyne, a thioalkyl group, and an alkylhydroxy group, or any combination thereof.

In some embodiments, each $R'_{1-5}$ represents 1 to 5 substituents independently selected from the group consisting of: hydrogen, an alkoxy group, a hydroxy group, a an amino group, a vinyl group, an allyl group, an alkyne, and an alkylhydroxy group, or any combination thereof.

In some embodiments, each R" independently comprises an alkyl, a substituted alkyl, or any combination thereof.

In some embodiments, the composition comprises the tetraaryl ammonium salt covalently bound to a sidechain and/or to a backbone of a polymer. In some embodiments, the tetraaryl ammonium salt covalently bound to a sidechain and/or to a backbone of a polymer via a substituent (e.g. $R'_{1-5}$).

In some embodiments, the tetraaryl ammonium salt is covalently bound to a sidechain of a polymer, thereby forming a direct adduct. In some embodiments, the tetraaryl ammonium salt is grafted to a sidechain of a polymer. In some embodiments, the tetraaryl ammonium salt is covalently bound to a sidechain of a polymer via a linker, thereby forming a linker based conjugate. In some embodiments, the tetraaryl ammonium salt is bound to a sidechain of a polymer by a click reaction. In some embodiments, a plurality of polymeric chains are crosslinked by a linker comprising the tetraaryl ammonium salt.

In some embodiments, any of a direct adduct and a linker based conjugate independently comprise a covalent bond, selected from the group consisting of: —O—, —S—, —P($R_1$")—, —N($R_1$")—, a disulfide bond, a phosphodiester, a phosphonate, a sulphonyl, a sulfonate, and a carboxyl acid derivate or any combination thereof.

In some embodiments, any of a direct adduct and a linker based conjugate independently comprise an oxime, a tetrazole, a Diels Alder adduct, a hetero Diels Alder adduct, an aromatic substitution reaction product, a nucleophilic substitution reaction product, a maleimide, a Huisgen-cycloaddition product, or a Michael reaction product.

In some embodiments, the polymer is a homopolymer comprising the tetraaryl ammonium salt covalently bound to a sidechain thereof. In some embodiments, the polymer is a copolymer. In some embodiments, the polymer is a block copolymer. In some embodiments, the polymer is a graft copolymer. In some embodiments, the polymer is a random copolymer. In some embodiments, the polymer is a block copolymer. In some embodiments, the polymer is an alternating copolymer. In some embodiments, the polymer is a branched polymer.

Non-limiting examples of polymers include but are not limited to: polycarbonate, polyurea, polyurethane, vinyl polymers, polyalkyl, polybutadiene, polyamide, PEG, polypropylene glycol, poly(tetrahydrofuran), polyacrylonitrile (PAN), polyisobutene, polyisoprene, polychloroprene, polystyrene (PS), polystyrene-coisoprene, poly(vinyl chloride) (PVC), polyethylene, polypropylene, polytetrafluoroethylene (PTFE), polyvinyl cyclohexane, poly(vinyl acetate) (PVA), methylated cellulose, polyvinylidene difluoride (PVDF), polyphenylene oxide (PPE), polysulfone or any combination thereof.

In some embodiments, the polymer is compatible with an electronic device such as an alkaline fuel cell, an alkaline battery or any other electrochemical device as described hereinbelow. In some embodiments, the polymer is stable under oxidizing and/or alkaline conditions.

In some embodiments, the polymer is a hydrophobic polymer.

In some embodiments, the direct adduct of the tetraaryl ammonium salt covalently bound to a sidechain of a polymer is represented by any of Formulae 9-11:

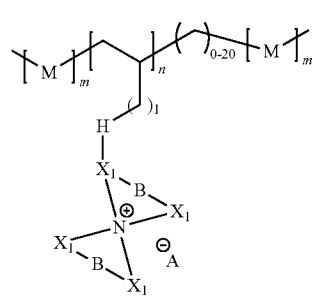

Formula 9

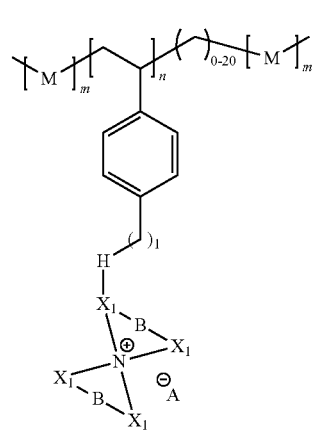

Formula 10

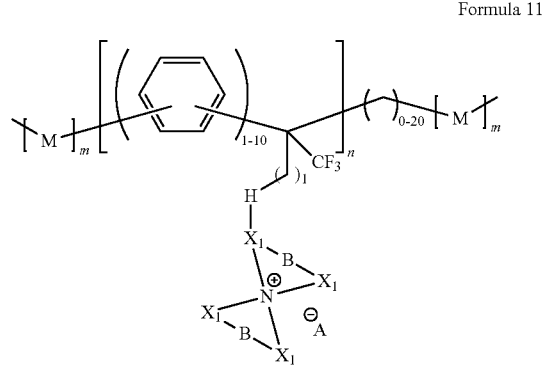

Formula 11 wherein:
M represents a repeating unit of a polymer, wherein the polymer is as described hereinabove;
H represents a heteroatom selected from the group consisting of: oxygen, nitrogen, sulfur, phosphorus;
l represents an integer, ranging from 0 to 20;
m represents an integer, ranging from 0 to 100,000;
n represents an integer, ranging from 1 to 100,000;
and $X_1$, B and $A^-$ are as described hereinabove.

In some embodiments, the direct adduct of the tetraaryl ammonium salt covalently bound to a sidechain of a polymer is represented by any of Formulae 12-14:

Formula 12

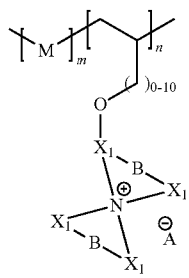

Formula 13

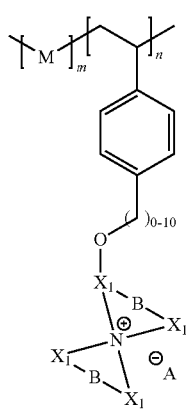

Formula 14

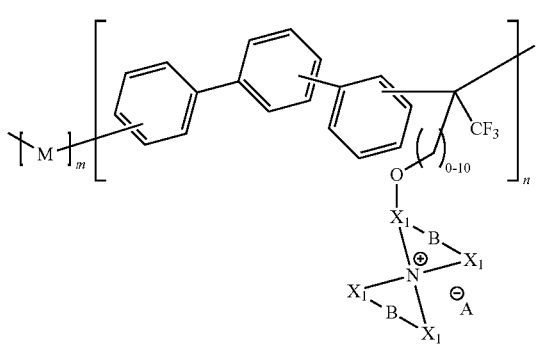

wherein M, $X_1$, B and $A^-$ are as described hereinabove.

In some embodiments, the direct adduct of the tetraaryl ammonium salt covalently bound to a sidechain of a polymer is represented by Formula 15:

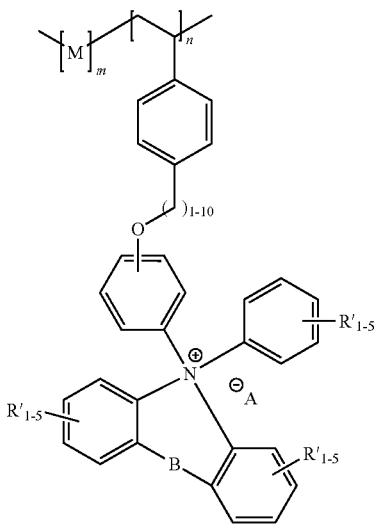

wherein $R'_{1-5}$, M, $X_1$, B and $A^-$ are as described hereinabove.

In some embodiments, M is polystyrene or is absent. In some embodiments, $R'_{1-5}$ is a hydroxy group or is absent.

In some embodiments, the direct adduct of the tetraaryl ammonium salt covalently bound to a sidechain of a polymer is represented by Formula 15a:

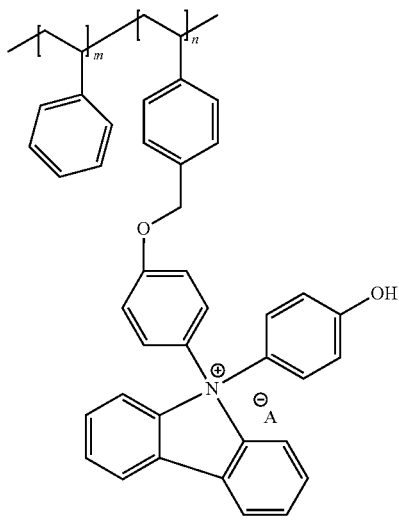

In some embodiments, the direct adduct of the tetraaryl ammonium salt covalently bound to a sidechain of a polymer is represented by Formula 16:

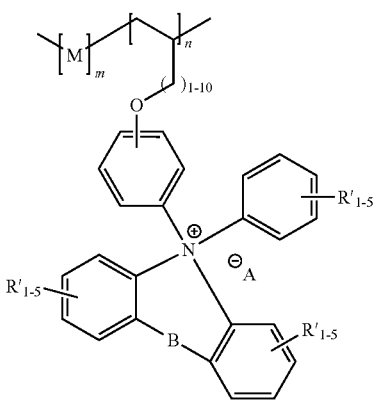

wherein R'$_{1-5}$, M, X$_1$, B and A$^-$ are as described hereinabove.

In some embodiments, M is polyethylene or is absent. In some embodiments, R'$_{1-5}$ is a hydroxy group or is absent.

In some embodiments, the direct adduct of the tetraaryl ammonium salt covalently bound to a sidechain of a polymer is represented by Formula 16a:

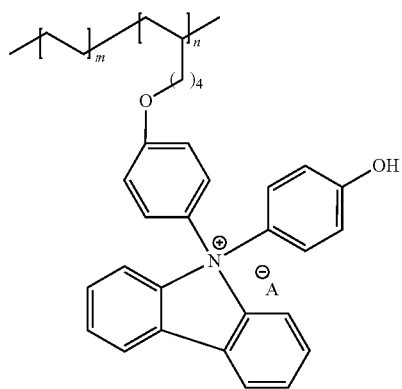

In some embodiments, the direct adduct of the tetraaryl ammonium salt covalently bound to a sidechain of a polymer is represented by Formula 17:

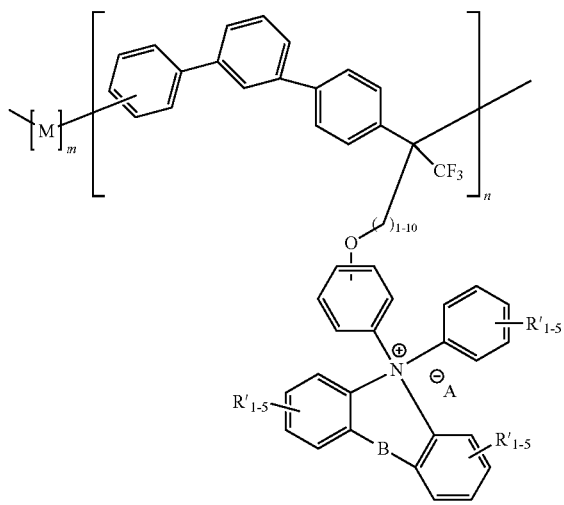

wherein R'$_{1-5}$, M, X$_1$, B and A$^-$ are as described hereinabove.

In some embodiments, M is absent. In some embodiments, R'$_{1-5}$ is a hydroxy group or is absent.

In some embodiments, the direct adduct of the tetraaryl ammonium salt covalently bound to a sidechain of a polymer is represented by Formula 17a:

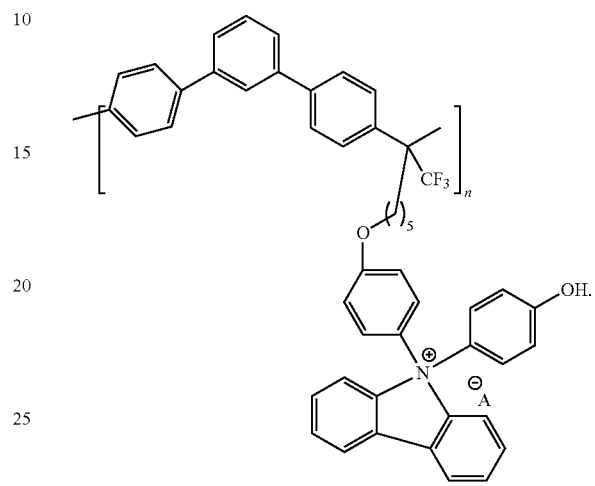

In some embodiments, the direct adduct of the tetraaryl ammonium salt covalently bound to a sidechain of a polymer is represented by Formula 17b:

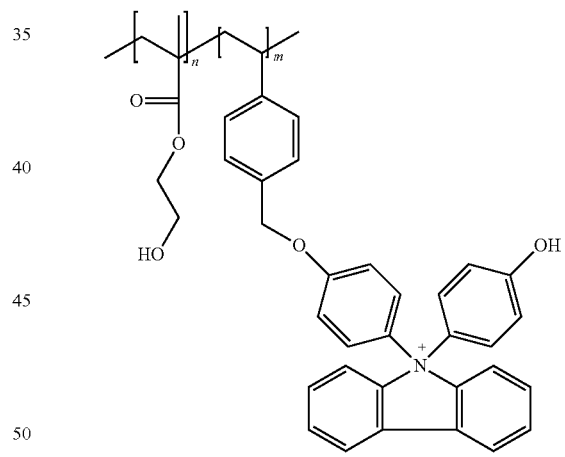

In some embodiments, a molar ratio of the polymer to the tetraaryl ammonium salt within the composition is in a range from 1:0.1 to 1:5, from 1:0.1 to 1:0.2, from 1:0.2 to 1:0.3, from 1:0.3 to 1:0.4, from 1:0.4 to 1:0.6, from 1:0.6 to 1:0.8, from 1:0.8 to 1:1, from 1:1 to 1:1.5, from 1:1.5 to 1:2, from 1:2 to 1:3, from 1:3 to 1:4, from 1:4 to 1:5, including any range or value therebetween.

Tetraaryl Ammonium Based Monomers and Copolymers Comprising Thereof

In another aspect of the invention, there is a composition comprising the tetraaryl ammonium salt covalently bound to a backbone of a polymer. In some embodiments, the tetraaryl ammonium salt covalently bound to a backbone and to a side chain of a polymer. In some embodiments, the backbone of a polymer is a copolymer selected from the group consisting of: a random copolymer, a block copolymer, and an alternating copolymer.

In some embodiments, the backbone of a copolymer comprises a first monomer copolymerized with a second monomer. In some embodiments, the first monomer is a tetraaryl ammonium salt based monomer. In some embodiments, the backbone of a copolymer comprises a tetraaryl ammonium salt based monomer copolymerized with a second monomer. In some embodiments, a tetraaryl ammonium salt based monomer is as described hereinbelow.

Non-limiting examples of a second monomer include but are not limited to: a diisocyanate, a diisothiocyanate, a vinyl based monomer (e.g. metacrylate, acrylate, styrene, divinyl benzene), a lactone (e.g. caprolactone), a bifunctional monomer (e.g. di-acyhalide, dicarboxylate), a dialkoxysilane or any combination thereof.

In some embodiments, the second monomer is a diisocyanate. In some embodiments, the second monomer is a hexamethylenediisocyanate.

In some embodiments, a tetraaryl ammonium based monomer is represented by any of Formulae 18, 19, 3a and 3c:

Formula 18

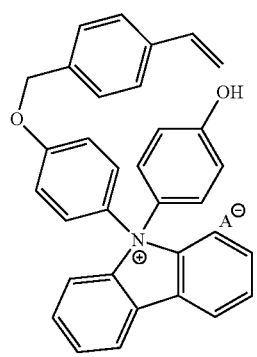

Formula 19

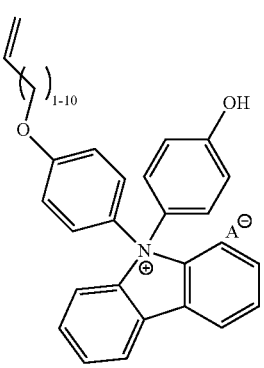

Formula 3a

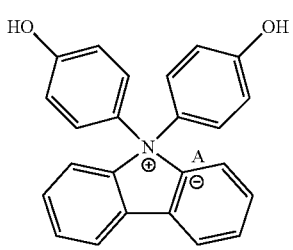

Formula 3c

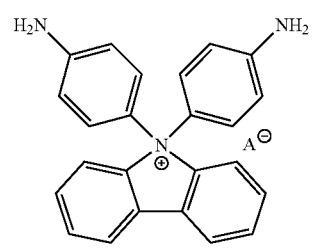

In some embodiments, the copolymer comprises monomers of diisocyante copolymerized with tetraaryl ammonium based monomers.

In some embodiments, the copolymer is represented by Formula 20:

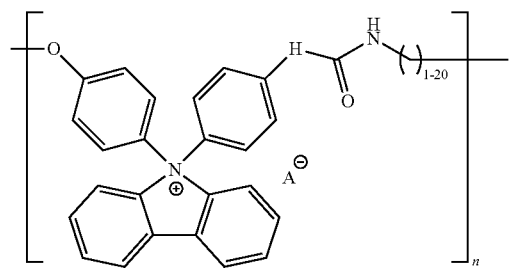

wherein H is oxygen or NH and n is from 1 to 100,000.

In some embodiments, the copolymer is represented by Formula 20a:

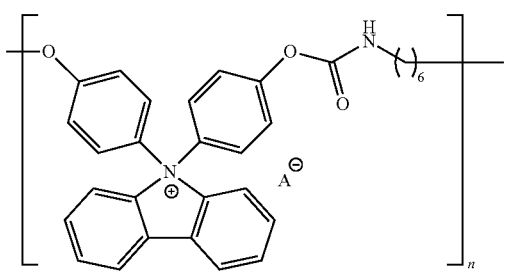

In some embodiments, the copolymer further comprises a third monomer copolymerized with the tetraaryl ammonium based monomer and the second monomer. In some embodiments, the copolymer further comprises an additional polymeric block, wherein the additional polymeric block is a polymerization product of a plurality of the third monomer. In some embodiments, the additional polymeric block comprises a polymer as described hereinabove.

In some embodiments, a molar ratio of the second monomer to the tetraaryl ammonium based monomer within the copolymer is in a range from 1:0.1 to 1:5, from 1:0.1 to 1:0.2, from 1:0.2 to 1:0.3, from 1:0.3 to 1:0.4, from 1:0.4 to 1:0.6, from 1:0.6 to 1:0.8, from 1:0.8 to 1:1, from 1:1 to 1:1.5, from 1:1.5 to 1:2, from 1:2 to 1:3, from 1:3 to 1:4, from 1:4 to 1:5, including any range or value therebetween.

In some embodiments, one or more compositions disclosed herein are stable under oxidizing and/or alkaline conditions.

As used hereinthroughout, the term "stable", or any grammatical derivative thereof, may refer to chemical stability. "Chemical stability" means that an acceptable percentage of degradation of the composition disclosed hereinthroughout produced by chemical pathways such as oxidation or alkaline degradation is formed. In particular, the composition is considered chemically stable if no more than about 10% degradation products are formed after e.g., 2 days of incubation at alkaline and/or oxidizing conditions.

In some embodiments, the composition is chemically stable under alkaline conditions. In some embodiments, the tetraaryl ammonium salt is stable under alkaline conditions. In some embodiments, the composition comprising the tetraaryl ammonium salt covalently bound to a sidechain of a polymer is chemically stable under alkaline conditions. In some embodiments, the copolymer is chemically stable under alkaline conditions. In some embodiments, the copolymer comprising the polymerization product of tetraaryl ammonium based monomers and optionally a plurality of second monomers is chemically stable under alkaline conditions.

In some embodiments, alkaline conditions comprise a pH value above 7. In some embodiments, alkaline conditions comprise a pH value ranging from 7 to 14, from 7 to 10, from 10 to 12, from 12 to 14.

In some embodiments, alkaline conditions correspond to an aqueous solution. In some embodiments, alkaline conditions correspond to an organic solution. In some embodiments, alkaline conditions correspond to a 0.5M hydroxide solution in a dry organic solvent (e.g. dimethylsulfoxide).

Figure 1B:
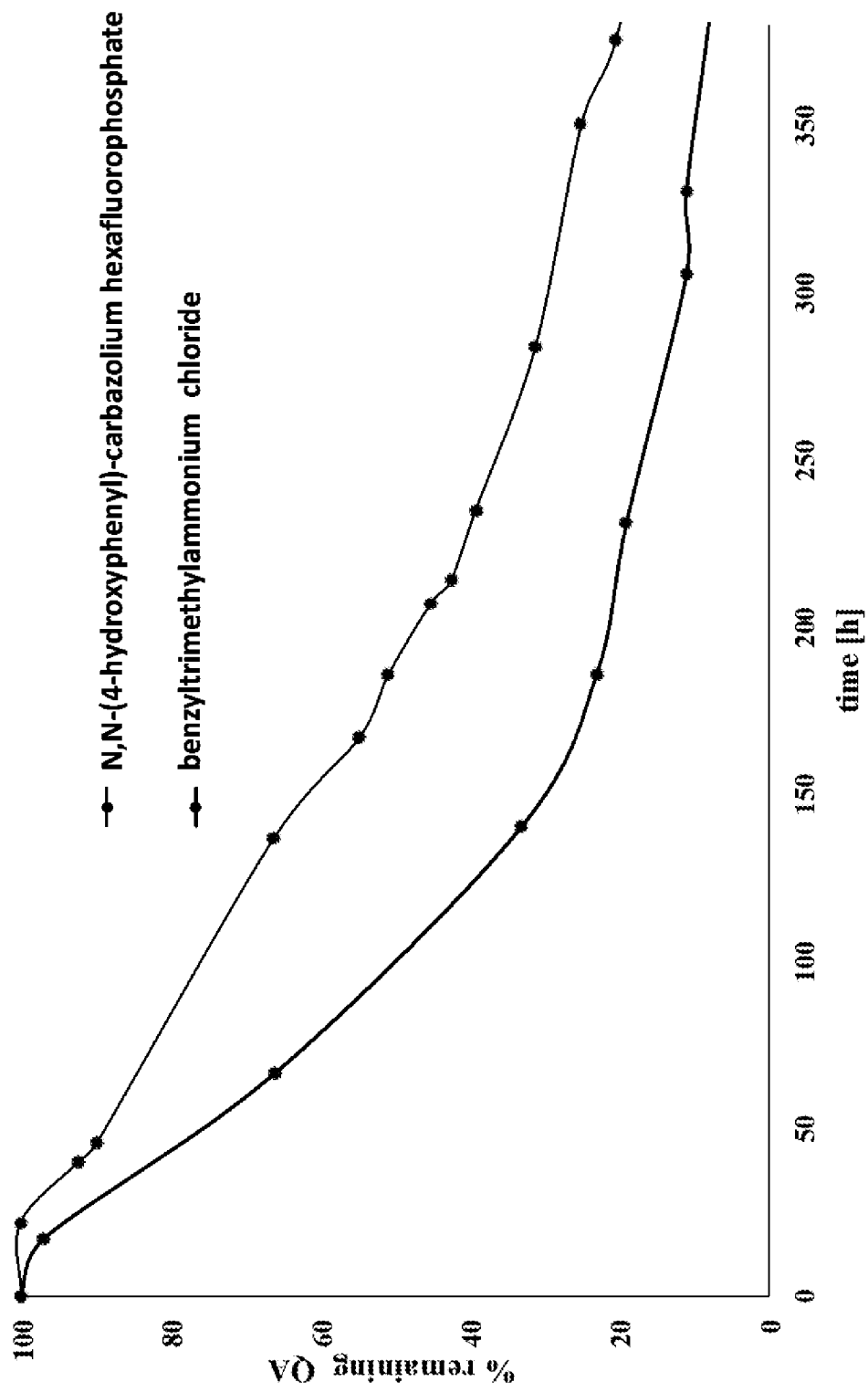
FIG. 1B is a graph showing a decomposition of N,N-(4-hydroxyphenyl)-carbazolium bromide and benzyltrimethylammonium chloride using 0.5 mol/L hydroxide in dry DMSO-d6. Hydration level of hydroxide is less than 0.2 water molecules/hydroxide, at room temperature.

The chemical stability of exemplary tetraaryl ammonium salts is represented by FIGS. 1A-B.

Method

In another aspect of the invention, there is a method for synthesizing a tetraaryl ammonium salt, comprising the steps of:
a) providing a biaryl compound comprising (i) a diazonium salt; (ii) a triaryl amine, wherein said (i) and (ii) are in a position suitable for intramolecular cyclization;
b) performing an intramolecular cyclization under suitable conditions, thereby obtaining the tetraaryl ammonium salt.

In some embodiments, the method further comprises the steps of:
a) providing a diaminobiaryl compound;
b) arylating at least one amino group of the diaminobiaryl compound to obtain a triaryl amine;
c) diazotizing a free amino group by reacting the triaryl amine with a diazotation compound, to obtain a diazonium salt, thereby obtaining the biaryl compound comprising the diazonium salt and the triaryl amine.

In some embodiments, the biaryl compound is any compound comprising a plurality of aryl rings bound head to tail. In some embodiments, the biaryl compound comprises a first aryl and a second aryl bound head to tail, such as biphenyl. In some embodiments, the biaryl compound comprises a triaryl amine bound to a first aryl and a diazonium salt bound to a second aryl.

In some embodiments, the biaryl compound comprises a fused ring system (e.g. phenanthrene) substituted by a triaryl amine and diazonium salt, wherein the triaryl amine and diazonium salt are positioned so as to enable an intramolecular cyclization.

In some embodiments, the biaryl compound comprises a triaryl amine and a diazonium salt at positions suitable for intramolecular cyclization. In some embodiments, the biaryl compound further comprises one or more substituents. In some embodiments, a triaryl amine and a diazonium salt are positioned so as to enable an intramolecular reaction. In some embodiments, a triaryl amine and a diazonium salt are positioned at a distance of at least 3 carbon-carbon bonds. In some embodiments, a triaryl amine and a diazonium salt are optionally in the same plane. In some embodiments, a triaryl amine and a diazonium salt are in the close proximity so as to enable a bonding interaction. In some embodiments, a triaryl amine and a diazonium salt are in the close proximity so as to enable a reaction. In some embodiments, a triaryl amine and a diazonium salt are positioned so as to enable a nucleophilic attack of the triaryl amine on the diazonium salt. In some embodiments, the position suitable for intramolecular cyclization is a 2,2' position.

In some embodiments, the biaryl compound is represented by Formula 21:

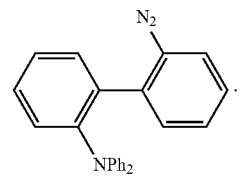

In some embodiments, the method comprises the step of providing a diaminobiaryl compound. In some embodiments, the diaminobiaryl compound is optionally mixed with an organic solvent, thereby resulting in a solution. In some embodiments, a molar concentration of the diaminoaryl compound within the solution is ranging from 0.01 to 3 mol/L, from 0.01 to 0.1 mol/L, from 0.1 to 0.5 mol/L, from 0.5 to 1 mol/L, from 1 to 1.5 mol/L, from 1.5 to 2 mol/L, from 2 to 2.5 mol/L, from 2.5 to 3 mol/L, including any range therebetween.

In some embodiments, an organic solvent is aprotic solvent. In some embodiments, an organic solvent is anhydrous solvent, with a weight per weight water content of less than 1%.

Non-limiting examples of appropriate solvents for the arylation step include but are not limited to: a halogenated hydrocarbon, acetonitrile, n-butyronitrile, iso-butyronitrile, a hydrocarbon (e.g. hexane, pentane, cyclohexane) or any combination thereof.

In some embodiments, the diaminobiaryl is a diaminobiphenyl compound represented by Formula 22:

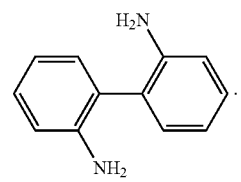

In some embodiments, the diaminobiaryl compound is optionally substituted.

In some embodiments, the diaminobiaryl compound is synthesized from a corresponding dinitro compound by hydrogenation. In some embodiments, the diaminoaryl compound is synthesized from a corresponding dinitro compound, in the presence of a catalyst (e.g. by Zn[0]) under acidic conditions.

In some embodiments, the dinitro compound is represented by Formula 23:

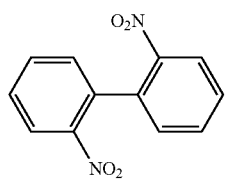 [SMILES: O=[N+]([O-])c1ccccc1-c1ccccc1[N+](=O)[O-]]

In some embodiments, at least one amino group of the diaminoaryl compound is optionally protected by a labile protecting group.

In some embodiments, the method comprises the step of arylating at least one amino group of the diaminobiaryl compound (also referred to as a "arylation step") to obtain a triaryl amine.

In some embodiments, arylating comprises reacting the diaminobiaryl compound with an aryl comprising a leaving group, optionally in the presence of a metal-based catalyst. In some embodiments, the aryl comprising a leaving group is a fused ring based compound. In some embodiments, the aryl comprising a leaving group is a biaryl based compound.

In some embodiments, the leaving group comprises any one of: a halo group, a nitro group, an azo group, a quaternary amino group. In some embodiments, the aryl comprising a leaving group is a haloaryl.

In some embodiments, the haloaryl is iodoaryl (e.g. iodobenzene). In some embodiments, the metal-based catalyst is a Cu(I) based catalyst, further comprising a bidentate ligand.

In some embodiments, Cu(I) based catalyst further comprises a bidentate ligand. In some embodiments, the ligand is sufficient to complex a Cu(I) atom. In some embodiments, the bidentate ligand is 1,10 phenantroline or a derivative thereof.

In some embodiments, reacting comprises mixing the diaminobiaryl comprising a leaving group compound with a haloaryl, in the presence of a Cu(I) based catalyst, thereby obtaining a reaction mixture. In some embodiments, reacting comprises mixing the solution of the diaminobiaryl comprising a leaving group compound with a haloaryl, in the presence of a Cu(I) based catalyst. In some embodiments, reacting further comprises adding a base (e.g. an alkoxylate salt, such as MeO⁻, tBuO⁻) to the solution of the diaminobiaryl comprising a leaving group compound prior to adding a haloaryl.

In some embodiments, reacting comprises heating the reaction mixture to a temperature ranging from 30 to 200° C., from 30 to 50° C., from 50 to 70° C., from 70 to 90° C., from 90 to 100° C., from 100 to 110° C., from 110 to 120° C., from 120 to 130° C., from 130 to 140° C., from 140 to 150° C., from 150 to 170° C., from 170 to 200° C., including any range therebetween.

In some embodiments, reacting comprises incubating the reaction mixture for a time period ranging from 0.1 to 24 h, from 0.5 to 1 h, from 1 to 1.5 h, from 1.5 to 2 h, from 2 to 2.5 h, from 2.5 to 3 h, from 3 to 3.5 h, from 3.5 to 4 h, from 4 to 5 h, from 5 to 6 h, from 6 to 7 h, from 7 to 10 h, from 10 to 24 h, including any range therebetween.

In some embodiments, the arylation step results in a formation of a diaryl amine, a triaryl amine or both. In some embodiments, the arylation step results in a selective substitution of only one amino group of the diaminobiaryl comprising a leaving group compound. In some embodiments, a compound(s) formed by the arylation step is represented by Formula 24:

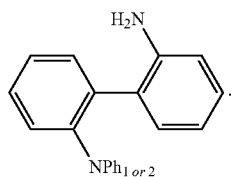

In some embodiments, a molar ratio of Cu(I) atom to the bidentate ligand within the Cu(I) based catalyst is at least 1:0.8, at least 1:1, at least 1:1.5, including any value therebetween.

In some embodiments, a molar ratio of the diaminobiaryl comprising a leaving group compound to the Cu(I) based catalyst is at least 1:0.01, at least 1:0.03, at least 1:0.05, at least 1:0.07, at least 1:0.1, at least 1:0.15, at least 1:0.2, at least 1:0.3, at least 1:0.5, including any value therebetween.

In some embodiments, a molar ratio of the diaminobiaryl comprising a leaving group compound to a haloaryl is at least 1:1, at least 1:1.2, at least 1:1.5, at least 1:1.7, at least 1:1.9, at least 1:2, at least 1:2.1, at least 1:2.2, at least 1:2.3, at least 1:2.4, at least 1:2.5, at least 1:2.6, at least 1:2.7, at least 1:3, at least 1:4, including any value therebetween.

In some embodiments, the arylation step results in a product mixture comprising di-, and tri-substituted amines. In some embodiments, the arylation step further comprises a purification step, so as to separate the product mixture. In some embodiments, the product mixture comprising di-, and tri-substituted amines is used for the subsequent synthetic step without a purification.

In some embodiments, the method comprises the step of diazotizing a free amino group (also referred to as a "diazotation step") by reacting the triaryl amine or the product mixture comprising the triaryl amine with a diazotation compound, to obtain a diazonium salt. In some embodiments, the triaryl amine is represented by Formula 24. In some embodiments, a free amino group corresponds to an unreacted amino group.

In some embodiments, a diazotation compound comprises a source of nitroso compound (N≡O⁺). In some embodiments, a diazotation compound comprises a nitrite salt, nitrous acid or both. In some embodiments, the diazotation step comprises a nitrite salt (e.g. NaNO₂) and an acid (e.g. HCl, acetic acid).

In some embodiments, the diazotation step is selective to the unreacted amino group. In some embodiments, the diazotation step further comprising mixing the triaryl amine or the product mixture comprising the same with an aqueous solvent prior to addition of the diazotation compound. In some embodiments, the diazotation step comprises cooling a reaction mixture to a temperature below 25° C. In some embodiments, the diazotation step is performed at a temperature ranging from −10 to 10° C.

In some embodiments, a diazonium salt is represented by Formula 21.

In some embodiments, the method comprises a step of intramolecular cyclization (also referred to as a "cyclization step") of the diazonium salt under appropriate conditions, thereby obtaining the tetraaryl ammonium salt. In some embodiments, the In some embodiments, the appropriate conditions comprise a temperature ranging from 20 to 100° C., from 20 to 30° C., from 30 to 35° C., from 35 to 40° C., from 40 to 45° C., from 45 to 50° C., from 50 to 55° C., from 55 to 60° C., from 60 to 70° C., from 70 to 80° C., from 80 to 100° C., including any range therebetween.

In some embodiments, the cyclization step comprises adding abase prior to heating the reaction mixture as described herein above. In some embodiments, the base is an inorganic base. In some embodiments, the base is a weak inorganic base.

In some embodiments, the base is selected from the group consisting of: urea, an acetate salt, a carbonate salt, ammonia, and basic alumina or any combination thereof. In some embodiments, the base is urea.

In some embodiments, the method further comprises a purification step to obtain a substantially pure tetraaryl ammonium salt.

Figure 2:
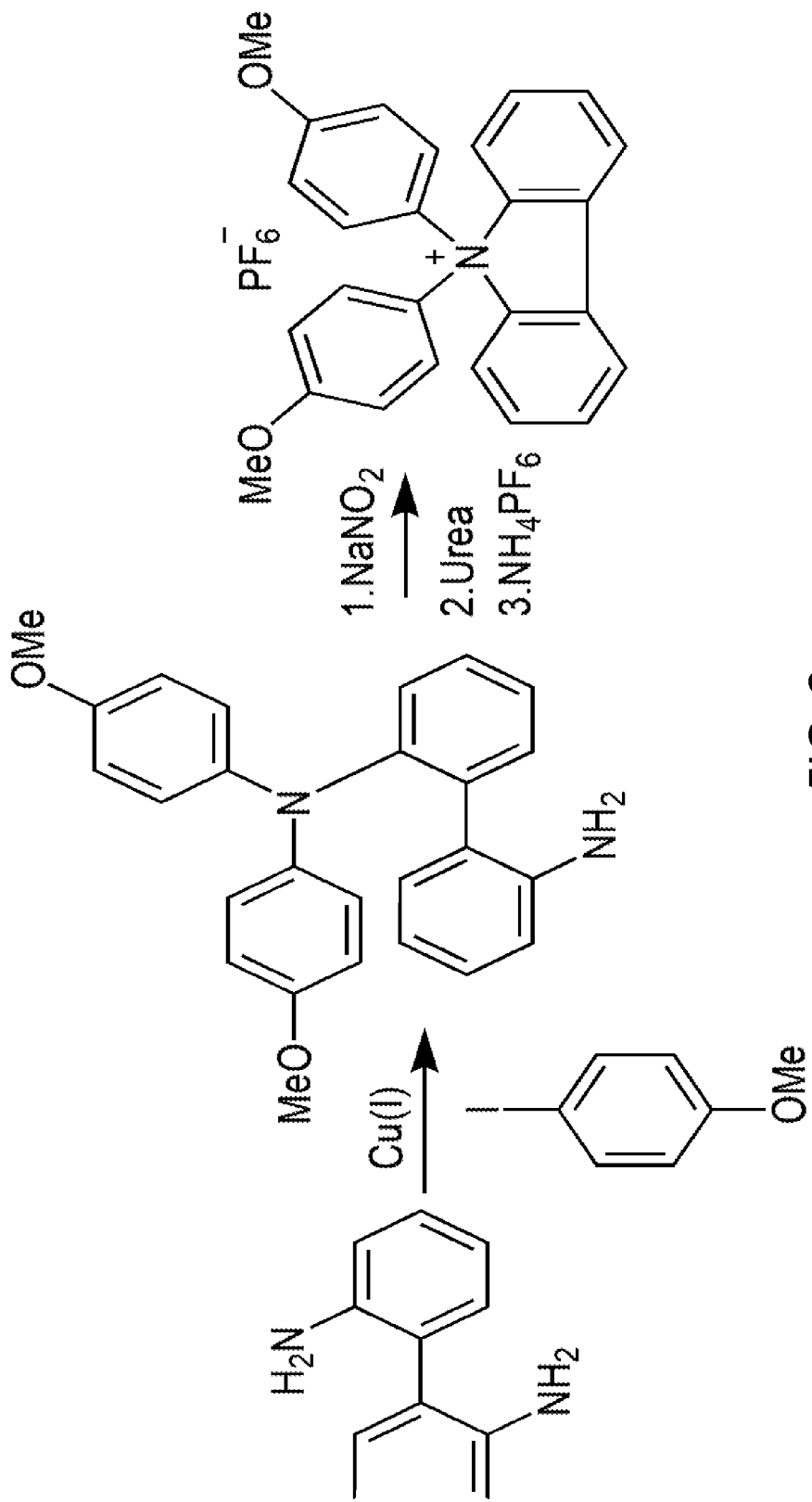
FIG. 2 shows a synthetic route for the preparation of N,N-ditolyl carbazolium hexafluorophosphate.
Figure 3:
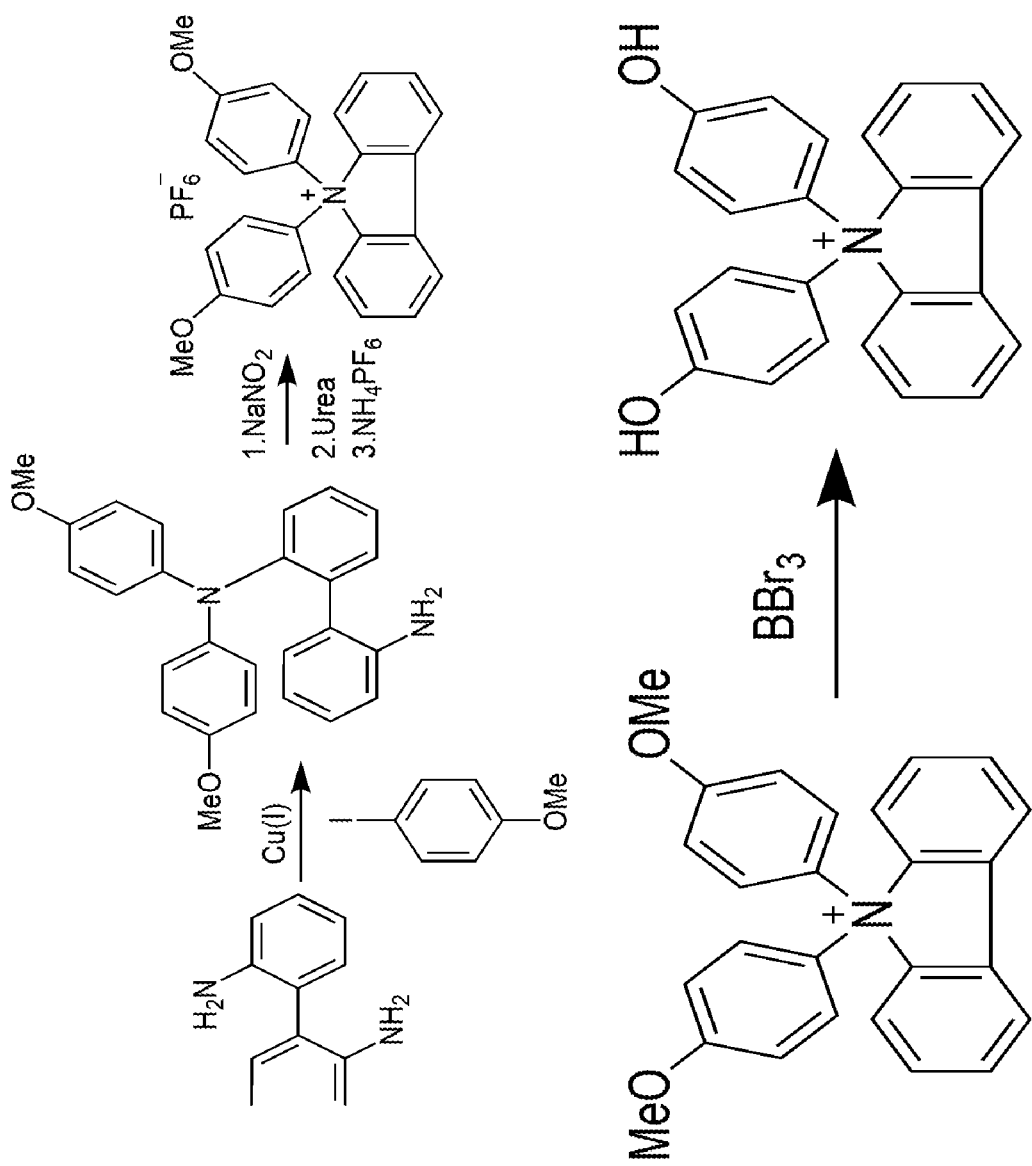
FIG. 3 shows a synthetic route for the preparation of N,N-(4-hydroxyphenyl)-carbazolium bromide.
Figure 4:
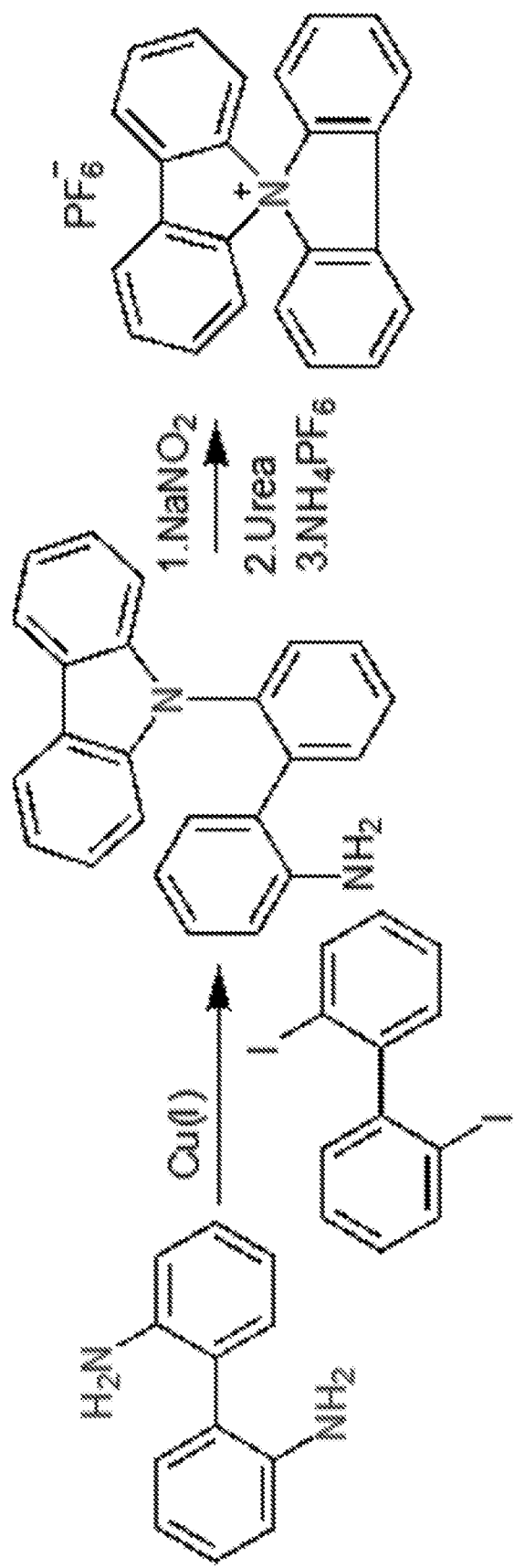
FIG. 4 shows a synthetic route for the preparation of 9,9-spiro bis-carbazolium hexafluorophosphate.

Exemplary methods for synthesizing tetraaryl ammonium salts are described in greater detail in the Examples section and illustrated by FIGS. 2-4.

In another aspect of the invention, there is a method for synthesizing a polymer bound to the tetraaryl ammonium salt. In some embodiments, a polymer is a copolymer comprising the tetraaryl ammonium salt bound to a side chain of the polymer, to a backbone of the polymer, or both.

In some embodiments, the method for synthesizing a polymer comprising the tetraaryl ammonium salt bound to a backbone of the polymer comprises:
  a. providing a tetraaryl ammonium based monomer and optionally a second monomer;
  b. mixing the tetraaryl ammonium based monomer and optionally the second monomer with a catalytic amount of a catalyst, thereby obtaining a reaction mixture;
  c. incubating the reaction mixture under appropriate conditions, thereby forming a polymeric backbone comprising the tetraaryl ammonium salt.

In some embodiments, the tetraaryl ammonium based monomer and the second monomer are as described hereinabove. In some embodiments, providing further comprises mixing the tetraaryl ammonium based monomer and optionally the second monomer with an organic solvent, thereby forming a solution of monomers.

In some embodiments, a catalyst is a tin(II)-based catalyst. In some embodiments, a catalyst is dibutyltin dilaurate.

In some embodiments, appropriate conditions comprise providing the reaction mixture to a temperature ranging from 30 to 200° C., from 30 to 50° C., from 50 to 70° C., from 70 to 90° C., from 90 to 100° C., from 100 to 110° C., from 110 to 120° C., from 120 to 130° C., from 130 to 140° C., from 140 to 150° C., from 150 to 170° C., from 170 to 200° C., including any range therebetween.

In some embodiments, appropriate conditions comprise reaction time ranging from 1 to 50 h, from 1 to 5 h, from 5 to 10 h, from 10 to 15 h, from 15 to 20 h, from 20 to 25 h, from 25 to 30 h, from 30 to 40 h, from 40 to 50 h, including any range therebetween.

In some embodiments, the copolymer comprising the tetraaryl ammonium salt bound to a backbone is represented by Formula 20a.

In some embodiments, the method for synthesizing a polymer comprising the tetraaryl ammonium salt bound to a sidechain of the polymer comprises:
  a. providing a polymer comprising a reactive group bound to a sidechain of the polymer;
  b. reacting the polymer with the tetraaryl ammonium salt; wherein the reactive group has a reactivity to the tetraaryl ammonium salt.

In some embodiments, the method further comprises adding abase prior to reacting the polymer with the tetraaryl ammonium salt.

In some embodiments, the tetraaryl ammonium salt comprises a substituent having a reactivity to the sidechain of the polymer. In some embodiments, the tetraaryl ammonium salt comprises a substituent having a reactivity to the reactive group bound to the sidechain of the polymer.

In some embodiments, the tetraaryl ammonium salt comprises a nucleophilic substituent having a reactivity to an electrophilic reactive group bound to the sidechain of the polymer, as represented by Formulae 3a and 3c.

In some embodiments, the method for synthesizing a polymer comprising the tetraaryl ammonium salt bound to a sidechain of the polymer comprises:
  a. providing a monomer comprising the tetraaryl ammonium salt;
  b. providing a catalyst;
  c. reacting the monomer under appropriate conditions, thereby forming the polymer comprising the tetraaryl ammonium salt bound to a sidechain thereof.

In some embodiments, a catalyst is a radical initiator. In some embodiments, a catalyst is a UV-light.

In some embodiments, providing a monomer further comprises mixing the monomer with a solvent.

In some embodiments, appropriate conditions are as described hereinabove.

In some embodiments, a polymer comprising the tetraaryl ammonium salt bound to a sidechain is represented by Formulae 9-17a.

Exemplary methods for synthesizing a polymer comprising the tetraaryl ammonium salt bound to a sidechain are described in greater detail in the Examples section and illustrated by FIGS. 5-9.

It will be apparent to those skilled in the art that the exact reaction conditions (such as reaction temperature, concentration, reagents ratios, mixing speed, and solvents) may vary, depending inter alia on the exact structure of reactants, a solvent, a desired yield, and on a setup of the manufacturing process.

Articles

In another aspect of the invention, there is an article comprising the composition of the invention.

In some embodiments, an article is for use as: an anion exchange membrane, and an anion conducting polymer.

In some embodiments, the article is characterized by a stability under alkaline conditions, as described herein above.

In some embodiments, the article being in form of an anion exchange membrane (AEM) is manufactured by a method comprising a mold casting, spin casting, and electrospinning. Exemplary method for manufacturing of an anion exchange membrane is described in greater detail in the Examples section. In some embodiments, the polymer of the invention may be blended or mixed with another polymer to form a composite membrane. Any suitable mixing or blending process may be used, and such methods are known in the art. Examples of materials that may be desirable to blend with the polymer according to exemplary embodiments of the invention include cation exchange polyelectrolytes, Teflon AF, silicone, inorganic particles such as $TiO_2$, $AlO_2$ and sol-gel materials.

In some embodiments, the membrane is formed by reinforcing a fabric with the polymer of the invention. A liquid mixture of the reactants can be applied to the fabric by casting the liquid monomer mixture onto the fabric or by soaking the fabric in the liquid mixture using individual pieces of fabric, multiple pieces of fabric arranged in stacks or with fabric from a roll in a continuous process. When heat is applied, the reaction between the reactants and polymerization will occur to form a crosslinked anion exchange membrane supported by a fabric.

In some embodiments, the anion exchange membrane as laminated or attached to at least one other anion exchange polyelectrolyte, another polymer or another type of material to form a composite membrane. This lamination may benefit the resulting properties (e.g., conductivity) of the membrane or may be provided for dimensional stability and/or handling efficiency. The substrate for lamination and the lamination method may, for example, be a porous substrate such as a non-woven fabric of e.g. polyethylene, polypropylene or polytetrafluoroethylene, or a microporous membrane obtainable by a stretch expansion method. The lamination method may be a method wherein a preliminarily prepared anion exchange membrane and a porous substrate are bonded by a so-called wet lamination method using a solution of a precursor of the anion exchanger as an adhesive.

The polymer of the invention can also be polymerized into a solid mass, processed and pulverized into small particles. The small particles can then be blended in an extruder and heated with a melted plastic, such as polyethylene or polypropylene. The plastic and ion exchange mixture can then be extruded into thin sheets of AEMs.

The AEMs formed from the polymer of the invention may be any suitable thickness. However, in some embodiments, the thickness of the AEM may be in a range of about 10 µm to about 1000 µm, and in some embodiments, in a range of about 20 µm to about 200 µm.

The AEMs may have any suitable ion exchange capacity. In some embodiments, the ion exchange capacity is in a range of about 0.1 to about 10 meq/g to about 10 meq/g, and in some embodiments, in a range of about 1 meq/g to about 5 meq/g.

The AEMs may have any suitable conductivity. In some embodiments, the conductivity is in a range of about $10^{-4}$ to about 1 S/cm, and in some embodiments, the conductivity is in a range of about $10^{-3}$ to about 0.3 S/cm.

AEMs are known and are used in various separation and purification applications, for example in electrodialysis, salt-splitting and metathesis. For example, anion exchange membranes described herein may be used in a method for concentrating an electrolyte by electrodialysis, wherein a cation exchange membrane or a hydrogen ion selective permeation membrane, and an anion exchange membrane, are alternately disposed between a cathode and an anode, and a voltage is applied while supplying an electrolyte solution. AEMs may also be used for water purification, as battery electrolytes and for use in carbon dioxide removal and absorption.

Alkaline Fuel Cells

The AEMs formed from the polymer described herein may be used in any suitable fuel cell, including alkaline fuel cells. A solid alkaline fuel cell according to the present invention typically includes two electrodes and an AEM defined above. In some embodiments, the electrodes for alkaline fuel cells are manufactured by a method of wet fabrication followed by sintering or by a method of dry fabrication through rolling and pressing components into the electrode structure. The electrode generally consists of a hydrophilic catalyzed layer on top of a porous conductive diffusion layer (homogeneous distribution of the fuel and oxidant, respectively), which is in turn bonded to a current collector that is usually metallic. In some embodiments, the electrode structure is built up from several layers obtainable by, e.g., sequential deposition of catalyst and catalyst electrolyte mixtures.

In the some alkaline fuel cells, air or oxygen may be used as the oxidizer and an alcohol, such as methanol, ethanol, or isopropanol, or an organic compound, such as dimethyl ether, may be used as the fuel in the form of a solution containing a water component. A water component contained in those fuels may be transported to the oxidizer in the heating/humidifying part to humidify the oxidizer. The structure, components and methods of forming and using fuel cells are known in the art as described in Unlit, M.; Zhou, J.; Kohl, P. A. Hybrid Polymer Electrolyte Fuel cells: Alkaline Electrodes with Proton Conducting Membrane. *Angewandte Chemie* 2010, 49, pp 1321-1323; Zhou, J; Unlu, M.; Anestis-Richard, I.; Kohl, P. A. Crosslinked, epoxy-based anion conductive membranes for alkaline membrane fuel cells. *Journal of Membrane Science* 2010, 350, pp 286-292; Unlu, M.; Zhou, J.; Kohl, P. A. Hybrid Anion and Proton Exchange Membrane Fuel Cells. *Journal of Physical Chemistry* 2009, 113, pp 11416-11423.

Further, the article of the present invention may be formed not only into a common flat shape but also into a bag, hollow fiber, hollow tube shape, or any other suitable shape. In some embodiments, the article has a shape of a film, a membrane, a tissue, a mesh, and a powder or any combination thereof.

In some embodiments, the article is in the form of alkaline fuel cell, alkaline water electrolyzer, alkaline redox-flow battery, metal-air battery, and a capacitor or any combination thereof.

General

As used herein the term "about" refers to [Symbol] 10%.

The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As used herein, the term "alkyl" describes an aliphatic hydrocarbon including straight chain and branched chain groups. The alkyl group has 1 to 100 carbon atoms, and more preferably 1-50 carbon atoms. Whenever a numerical range; e.g., "1-100", is stated herein, it implies that the group, in this case the alkyl group, may contain 1 carbon atom, 2 carbon atoms, 23 carbon atoms, etc., up to and including 100 carbon atoms. In the context of the present invention, a "long alkyl" or "high alkyl" is an alkyl having at least 10, or at least 15 or at least 20 carbon atoms in its main chain (the longest path of continuous covalently attached atoms), and may include, for example, 10-100, or 15-100 or 20-100 or 21-100, or 21-50 carbon atoms. A "short alkyl" or "low alkyl" has 10 or less main-chain carbons. The alkyl can be substituted or unsubstituted, as defined herein.

The term "alkyl", as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "cycloalkyl" or "cycloalkane" describes an all-carbon monocyclic or fused ring (i.e., rings that share an adjacent pair of carbon atoms) group where one or more of the rings does not have a completely conjugated pi-electron system. The cycloalkyl group may be substituted or unsubstituted, as indicated herein.

The term "aryl", "aryl ring" or "aromatic" describes an all-carbon monocyclic or fused-ring polycyclic (i.e., rings which share adjacent pairs of carbon atoms) groups having a completely conjugated pi-electron system. The aryl ring may have one or more heteroatoms within the ring structure. The aryl group may be substituted or unsubstituted, as indicated herein.

The term "alkoxy" describes both an —O-alkyl and an —O-cycloalkyl group, as defined herein.

The term "aryloxy" describes an —O-aryl, as defined herein.

Each of the alkyl, cycloalkyl and aryl groups in the general formulas herein may be substituted by one or more substituents, whereby each substituent group can independently be, for example, halide, alkyl, alkoxy, cycloalkyl, alkoxy, nitro, amine, hydroxyl, thiol, thioalkoxy, thiohydroxy, carboxy, amide, aryl and aryloxy, depending on the substituted group and its position in the molecule. Additional substituents are also contemplated.

The term "halide", "halogen" or "halo" describes fluorine, chlorine, bromine or iodine.

The term "haloalkyl" describes an alkyl group as defined herein, further substituted by one or more halide(s).

The term "hydroxyl" or "hydroxy" describes a —OH group.

The term "thiohydroxy" or "thiol" describes a —SH group.

The term "thioalkoxy" describes both an —S-alkyl group, and a —S-cycloalkyl group, as defined herein.

The term "thioaryloxy" describes both an —S-aryl and a —S-heteroaryl group, as defined herein.

The term "amine" describes a —NR'R" group, with R' and R" as described herein.

The term "heteroalicyclic" or "heterocyclyl" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofuran, tetrahydropyrane, morpholino and the like.

The term "carboxy" or "carboxylate" describes a —C(=O)—OR' group, where R' is hydrogen, alkyl, cycloalkyl, alkenyl, aryl, heteroaryl (bonded through a ring carbon) or heteroalicyclic (bonded through a ring carbon) as defined herein. The term "amide" as used herein encompasses C-amide and N-amide.

The term "C-amide" describes a —C(O)NR'R" end group or a —C(O)NR'-linking group, as these phrases are defined hereinabove, where R' and R" are as defined herein.

The term "N-amide" describes a —NR"C(O)R' end group or a —NR'C(O)— linking group, as these phrases are defined hereinabove, where R' and R" are as defined herein.

The term "carboxylic acid derivative" or "acyl" encompasses carboxy, amide, carbonyl, anhydride, carbonate ester, and carbamate.

The term "carbonyl" describes a —C(=O)—R' group, where R' is as defined hereinabove.

The above-terms also encompass thio-derivatives thereof (thiocarboxy and thiocarbonyl).

The term "thiocarbonyl" describes a —C(=S)—R' group, where R' is as defined hereinabove.

A "thiocarboxy" group describes a —C(=S)—OR' group, where R' is as defined herein.

A "sulfinyl" group describes an —S(=O)—R' group, where R' is as defined herein.

A "sulfonyl" or "sulfonate" group describes an —S(=O)$_2$—R' group, where Rx is as defined herein.

A "carbamyl" or "carbamate" group describes an —OC(=O)—NR'R" group, where R' is as defined herein and R" is as defined for R'.

A "nitro" group refers to a —NO$_2$ group.

A "cyano" or "nitrile" group refers to a —C≡N group.

As used herein, the term "azide" refers to a —N$_3$ group.

The term "sulfonamide" refers to a —S(=O)$_2$—NR'R" group, with R' and R" as defined herein.

The term "phosphonyl" or "phosphonate" describes an —O—P(=O)(OR')$_2$ group, with R' as defined hereinabove.

The term "phosphinyl" describes a —PR'R" group, with R' and R" as defined hereinabove.

The term "alkaryl" or "arylalkyl" describes an alkyl, as defined herein, which substituted by an aryl, as described herein. An exemplary alkaryl is benzyl.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted by one or more substituents, as described hereinabove. Representative examples are thiadiazole, pyridine, pyrrole, oxazole, indole, purine and the like.

As used herein, the terms "halo" and "halide", which are referred to herein interchangeably, describe an atom of a halogen, that is fluorine, chlorine, bromine or iodine, also referred to herein as fluoride, chloride, bromide and iodide.

The term "haloalkyl" describes an alkyl group as defined above, further substituted by one or more halide(s).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Example 1

Synthesis of N,N-Ditolyl Carbazolium Hexafluorophosphate

In an oven dried Schlenk flask (50 mL), 2,2'-biphenyl-diamine (1.00 g, 5.42 mmol) and 4-iodotoluene (2.367 g, 10.84 mmol) were dissolved in xylenes (15 mL) and the flask deoxygenated using 3 freeze-pump-thaw cycles. The flask was backfilled with argon. KOtBu (1.33 g, 11.92 mmol) was then added and the mixture left for 10 min stirring at room temperature. Then, CuI (0.201 g, 1.084 mmol) and 1,10-phenanthroline (0.195 g, 1.084 mmol) were added and the mixture was stirred for 3.5 h at 125° C. The mixture was allowed to cool to room temperature and was filtered. The solids were washed with chloroform and then dissolved in 25% NH$_4$OH (30 mL). The aqueous phase was then extracted with CHCl$_3$. The organic phases were combined, and the solvents evaporated. The concentrated paste was re-dissolved in CHCl$_3$ and extracted with NH$_4$OH until no blue color was observed. To separate the unreacted diamine, HCl was added to the organic phase and extracted. The organic phase was then washed with saturated NaHCO$_3$, dried over Na$_2$SO$_4$, filtered and evaporated. At this stage, the mixture could be used for the next step without further purification. Part of the solid (0.3 g, 0.824 mmol) was dissolved in glacial acetic acid (4 mL) in an Erlenmeyer (25 mL). The solution was cooled to 0° C. in an ice bath. The frozen acetic acid is crushed with a metallic spatula before NaNO$_2$ (0.3 g, 4.35 mmol) in water (0.4 mL) was added, and the slurry mechanically stirred for 20 min. Urea (0.23 g, 3.8 mmol) was added next, and the mixture stirred for 1 h at 40° C. The solvents were evaporated, and the residue dissolved in CHCl$_3$. The non-soluble part was filtered and washed with CHCl$_3$. The filtrate was concentrated in vacuo and separated using extraction with water and ether. Water and acetic acid were removed in vacuo by freeze-drying. The acetate was converted to the hexafluorophosphate by addition to a saturated solution of NH$_4$PF$_6$. The salt precipitates and the solids are filtered and washed with water and ether. The red brown solids are then dried under vacuum (220 mg, 54% yield). The reaction scheme is represented by FIG. 2.

Example 2

Stability Test of Quaternary Ammonium Salts and Polymers

Two solutions are prepared in the dry glove box and mixed for each test at t=0: (1) dry KOH in 18-crown-6 (0.5 mmol, prepared by water titration of potassium) dissolved in DMSO-d6 (400 µL); and (2) quaternary ammonium salt (0.035 mmol) and mesitylene (1.5 µL, used as internal standard) dissolved in DMSO-d6 (100 µL). For experiments with λ>0, the DMSO-d6 used to dissolve the quaternary ammonium was reduced by the volume of water needed to achieve the desired λ. This water is added to (1) before the addition of the QA solution (2). As an example, the stability of the above molecules in hydroxide at room temperature is shown in FIG. 1A and FIG. 1B.

Example 3

Synthesis of N,N-(4-Hydroxyphenyl)-Carbazolium Hexafluorophosphate

N,N-(4-methoxyphenyl)-carbazolium hexafluorophosphate is prepared by the same procedure as for Example 1, but using 4-iodoanisole instead of 4-iodotoluene.

Subsequently, N,N-(4-methoxyphenyl)-carbazolium hexafluorophosphate (525 mg, 1 mmol) is dissolved in dry CH$_2$Cl$_2$ in a glove box, and added, slowly, to a BBr$_3$ 1.0 M solution in CH$_2$Cl$_2$ (10 mL). The reaction is stirred at room temperature for 3 days. Methanol is added slowly to neutralize excess BBr$_3$, and the whole solution is evaporated. Ethyl acetate is washed, leaving the solid product clean as a white solid. This is filtered and dried under vacuum (253 mg, 58% yield). The reaction scheme is represented by FIG. 3.

Example 4

Synthesis of 9,9-Spiro Bis-Carbazolium Hexafluorophosphate

The compound is prepared using the same procedure as for Example 1, using 2,2'-diiodobiphenyl instead of 4-iodotoluene.

Example 5

Synthesis of Polyurethane Containing Carbazolium Groups in the Main Chain

N,N-(4-hydroxyphenyl)-carbazolium bromide (432 mg, 1 mmol) and hexamethylenediisocyanate (168 mg, 1 mmol) are mixed in THF (5 mL). A drop of dibutyl-tin laurate is added, and the solution is refluxed for 24 h. The solvent is evaporated, providing the desired polyurethane as a rubbery solid.

Example 6

Synthesis of Polystyrene Containing Carbazolium Groups in the Side-Chain

Figure 5:
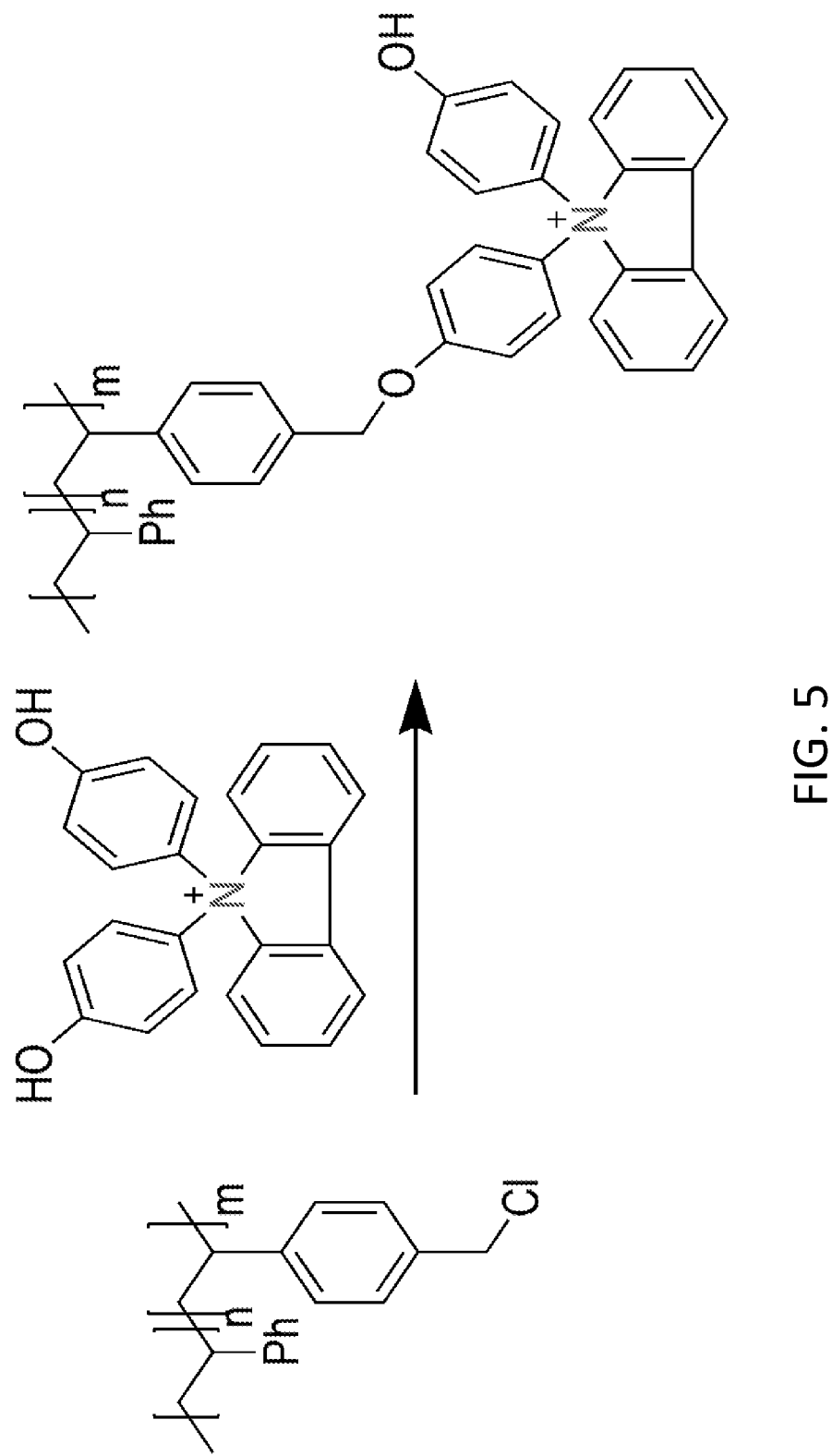
FIG. 5 shows a synthetic route for the preparation of polystyrene polymer comprising carbazolium groups as sidechains by direct grafting.

A copolymer of styrene and 4-chloromethyl styrene (1:1) is prepared using NMP. The polymer is than dissolved in a DMSO solution containing excess N,N-(4-hydroxyphenyl)-carbazolium bromide and potassium t-butoxide. The solution is mixed at 90 C for 1 day. The polymer is precipitated by pouring the solution into ether. The solid polymer is washed with water until pure. The reaction scheme is represented by FIG. 5.

Example 7

Figure 6:
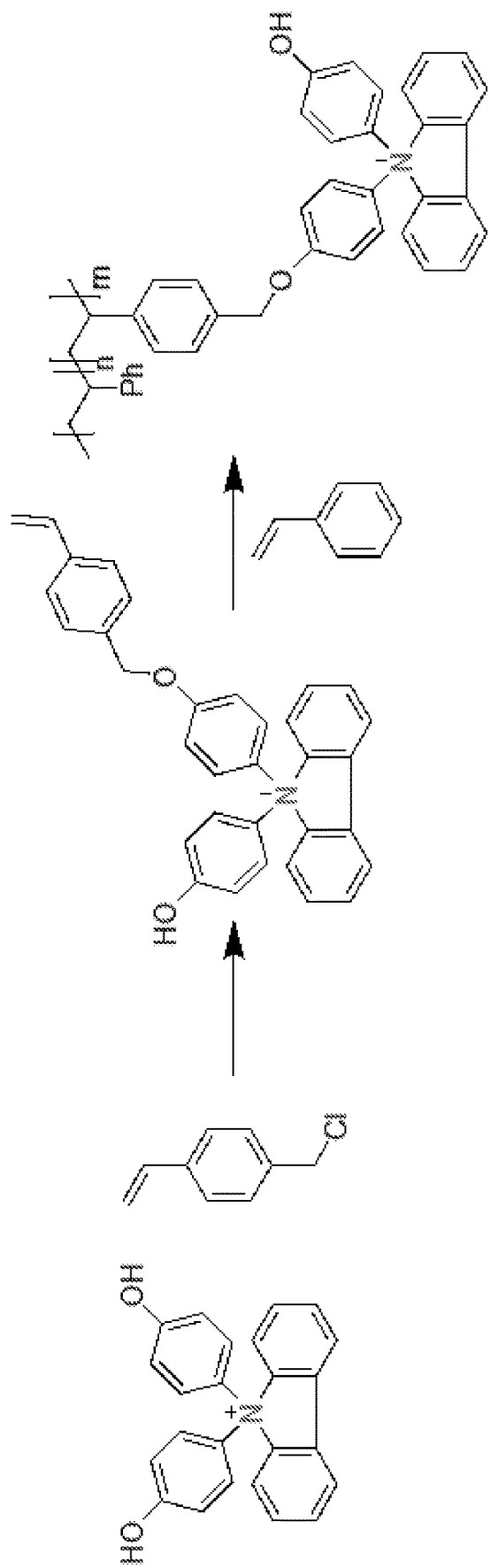
FIG. 6 shows a synthetic route for preparation of polystyrene polymer comprising carbazolium groups as sidechains by copolymerization.

Synthesis of Polystyrene Membrane Containing Carbazolium Groups in the Side-Chain by Co-Polymerization These membranes can be prepared by two different approaches:
1. Direct casting of the polymer described in Example 6: solvent cast from water, or hot press above the Tg.
2. Direct polymerization of monomers in mold:
Direct polymerization approach:
N,N-(4-hydroxyphenyl)-carbazolium bromide (432 mg, 1 mmol) and 4-chloromethylstyrene (100 mg, 0.66 mmol) are mixed with KOH in THF (5 mL). The mixture is heated to reflux for 3 days. The THF is evaporated and the solid washed dissolved in methanol and filtered. The filtrate is then evaporated. Styrene (as desired) is added to the solid, and the mixture is dissolved in small amounts of t-BuOH. The solution is poured into a mold of the desired membrane shape and cured using a strong UV source until a brittle solid membrane is obtained. The reaction scheme is represented by FIG. 6.

Example 8

Figure 7:
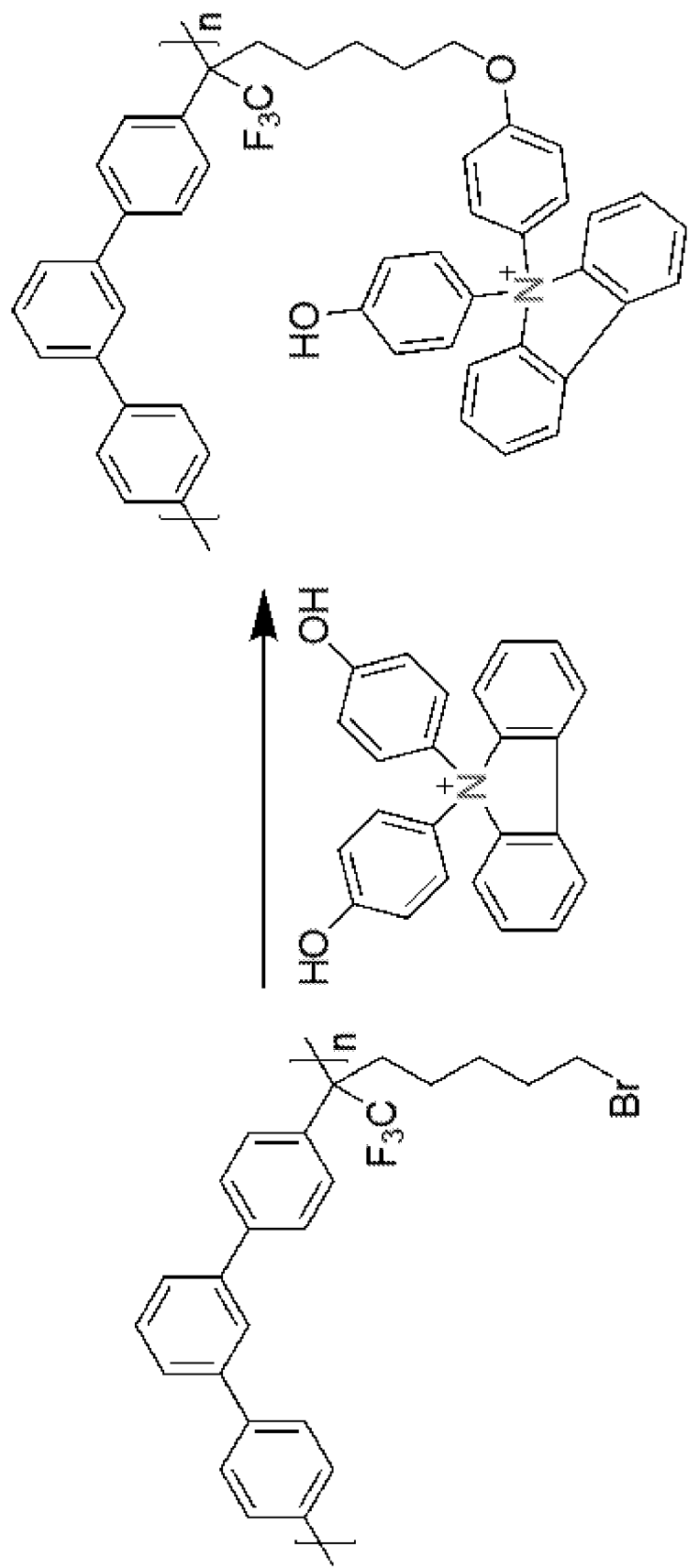
FIG. 7 shows a synthetic route for the preparation of poly(m-terphenylene) polymer comprising carbazolium groups as sidechains.

Synthesis of Poly(m-Terphenylene) Membrane Containing Carbazolium Groups in the Side-Chain A copolymer of 7-bromo-1,1,1-trifluoroheptan-2-one and m-terphenyl (m-TPN) obtained commercially is cast into a membrane using dimethyl acetamide as a solvent. The membrane is added to a DMSO solution containing excess N,N-(4-hydroxyphenyl)-carbazolium bromide and potassium t-butoxide. The solution is mixed at 90 C for 2 weeks. The membrane is than washed continuously with water. The reaction scheme is represented by FIG. 7.

Example 9

Figure 8:
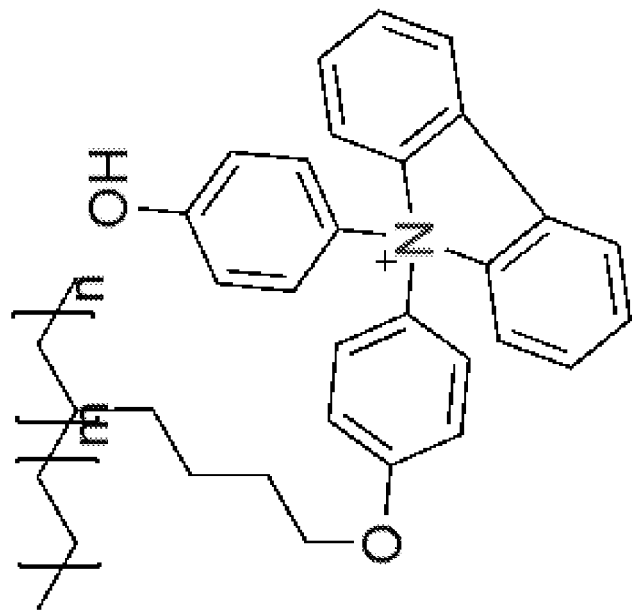
FIG. 8 shows a synthetic route for the preparation of polyethylene copolymer comprising carbazolium groups as sidechains.
Figure 8:
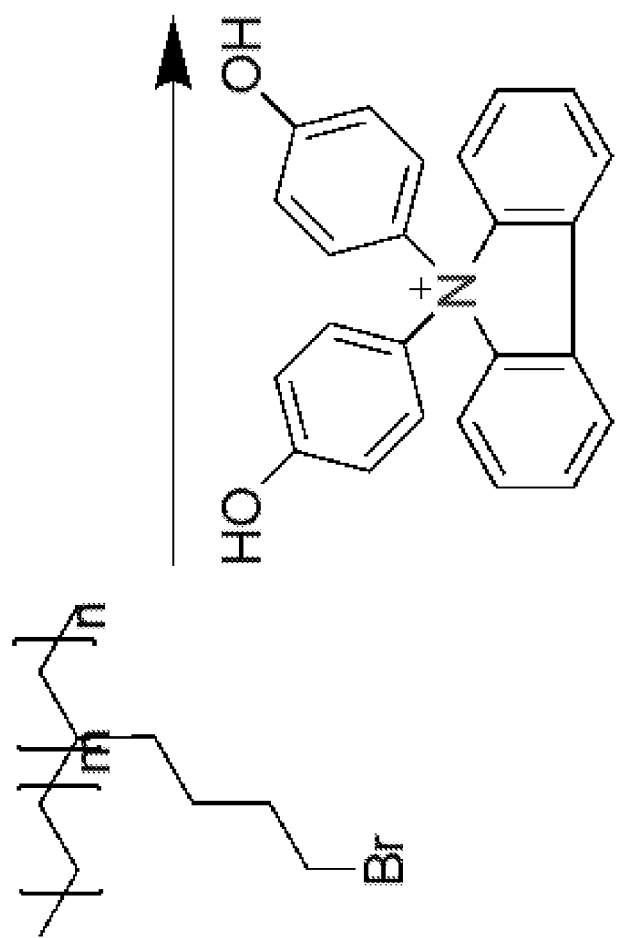

Synthesis of Polyethylene Membrane Containing Carbazolium Groups in the Side-Chain A polyethylene membrane functionalized with alkyl bromide groups was obtained commercially. The membrane is added to a DMSO solution containing excess N,N-(4-hydroxyphenyl)-carbazolium bromide and potassium t-butoxide. The solution is mixed at 90 C for 2 weeks. The membrane is than washed continuously with water. The reaction scheme is represented by FIG. 8.

Example 10

Figure 9:
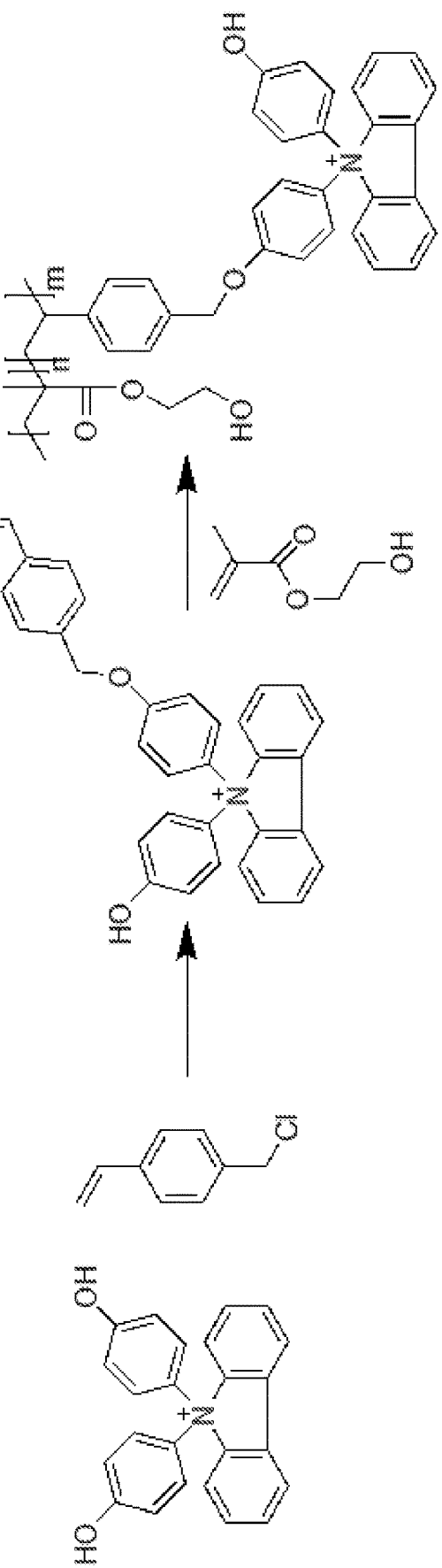
FIG. 9 shows a synthetic route for the preparation of methacrylate-based copolymer comprising carbazolium groups as sidechains.

Synthesis of Methacrylic Co-Polymer Based Membrane Containing Carbazolium Groups in the Side-Chain These membranes can be prepared by two different approaches:
1. Direct casting of the polymer described in Example 7: solvent cast from water, or hot press above the Tg.
2. Direct polymerization of monomers in mold:
Direct Polymerization of Monomers in Mold:
N,N-(4-hydroxyphenyl)-carbazolium bromide (432 mg, 1 mmol) and 4-chloromethylstyrene (100 mg, 0.66 mmol) are mixed with KOH in THF (5 mL). The mixture is heated to reflux for 3 days. The THF is evaporated and the solid washed dissolved in methanol and filtered. The filtrate is then evaporated. 2-hydroxyethylmethacrylate (1 equivalent), benzoyl peroxide (7.5 mg) and N,N-dimethylaniline (5 µl) and 2 drops of DMF are added and the mixture is mixed until all the carbazolium salt dissolved. The solution is degassed and inserted into a glove box where it is poured into a Teflon mold of the desired membrane shape. The mold is heated to 50 C for 12 hours and then taken out of the mold. The reaction scheme is represented by FIG. 9.

What is claimed is:

1. A composition comprising a tetraaryl ammonium salt represented by Formula 5:

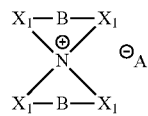

wherein:
each B represents independently a bond, or is absent;
$A^-$ is a counter anion; and
each $X_1$ independently comprises an all-carbon aryl ring, a substituted all-carbon aryl ring, a heteroaryl ring, or a substituted heteroaryl ring, wherein each of said substituted aryl ring and said substituted heteroaryl ring comprises one or more substituents selected from the group consisting of: a hydroxy group, an alkoxy group, an amino group, an aminoalkyl group, a guanidine group, a thioalkoxy group, a mercapto group, a cyano group, a haloalkyl group, an arylalkyl group, a nitro group, an azo group, a heteroalkyl, a sulfonate group, a sulfinyl group, a vinyl group, an allyl group, an alkyne, a thioalkyl group, an alkylhydroxy group, a keto group, a carboxylic acid derivative, and a sulfone group or any combination thereof;

and wherein:

at least one B is a bond;

with the proviso that at least one of said $X_1$ is selected from the group consisting of a substituted all-carbon aryl ring, an unsubstituted heteroaryl ring, and a substituted heteroaryl ring, wherein said substituted all-carbon aryl ring comprises one or more substituents selected from a hydroxy group, an alkoxy group, an amino group, an aminoalkyl group, an alkyhydroxy group, and any combination thereof.

2. The composition of claim 1, wherein each of said $X_1$ is independently selected from the group consisting of a substituted all-carbon aryl ring, an unsubstituted heteroaryl ring, and a substituted heteroaryl ring; and wherein one B represents a bond and the other B is absent.

3. The composition of claim 1, wherein each of said $X_1$ is independently selected from the group consisting of a substituted all-carbon aryl ring, an unsubstituted heteroaryl ring, and a substituted heteroaryl ring; and wherein each B independently represents a bond.

4. A composition comprising a tetraaryl ammonium salt covalently bound to a polymer, wherein said tetraaryl ammonium salt is represented by Formula 5:

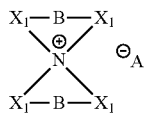

wherein:

each B represents independently a bond, or is absent;

$A^-$ is a counter anion; and each $X_1$ independently comprises an all-carbon aryl ring, a substituted all-carbon aryl ring, a heteroaryl ring, or a substituted heteroaryl ring, wherein each of said substituted aryl ring and said substituted heteroaryl ring comprises one or more substituents selected from the group consisting of: a hydroxy group, an alkoxy group, an amino group, an aminoalkyl group, a guanidine group, a thioalkoxy group, a mercapto group, a cyano group, a haloalkyl group, an arylalkyl group, a nitro group, an azo group, a heteroalkyl, a sulfonate group, a sulfinyl group, a vinyl group, an allyl group, an alkyne, a thioalkyl group, an alkylhydroxy group, a keto group, a carboxylic acid derivative, and a sulfone group or any combination thereof;

and wherein:

at least one B is a bond;

with the proviso that at least one of said $X_1$ is selected from the group consisting of a substituted all-carbon aryl ring, an unsubstituted heteroaryl ring, and a substituted heteroaryl ring, wherein said substituted all-carbon aryl ring comprises one or more substituents selected from a hydroxy group, an alkoxy group, an amino group, an aminoalkyl group, an alkyhydroxy group, and any combination thereof.

5. The composition of claim 4, wherein said tetraaryl ammonium salt is covalently bound to a polymer backbone, to a polymer sidechain, or to both.

6. The composition of claim 4, wherein said polymer is selected from a polycarbonate, a polyurea, a polyurethane, a vinyl polymers, a polyalkyl, a polybutadiene, a polyamide, a PEG, a polypropylene glycol, a poly(tetrahydrofuran), a polyacrylonitrile (PAN), a polyisobutene, a polyisoprene, a polychloroprene, a polystyrene (PS), a polystyrene-coisoprene, a poly(vinyl chloride) (PVC), a polyethylene, a polypropylene, a polytetrafluoroethylene (PTFE), a polyvinyl cyclohexane, a poly(vinyl acetate) (PVA), a methylated cellulose, a polyvinylidene difluoride (PVDF), a polyphenylene oxide (PPE), a polysulfone or and any combination thereof.

7. The composition of claim 4, wherein a molar ratio of said polymer to said tetraaryl ammonium salt within said composition is in a range from 1:0.1 to 1:5.

8. The composition of claim 4, wherein said composition maintains its chemical identity at a pH ranging from 1 to 14.

9. A method of synthesizing the tetraaryl ammonium salt of claim 1, the method comprising:

performing an intramolecular cyclization of a biaryl compound, wherein said biaryl compound comprises (i) a diazonium salt; and (ii) a triaryl amine, wherein said intramolecular cyclization is performed at a temperature in a range of from 20 to 100° C.; and/or while adding a base, and wherein said (i) said diazonium salt and (ii) said triaryl amine are positioned at a distance of at least 3 carbon-carbon bonds, to thereby obtain the tetraaryl ammonium salt.

10. The method of claim 9, further comprising, prior to performing said intramolecular cyclization:

arylating at least one amino group of a diaminobiaryl compound to obtain a triaryl amine; and diazotizing a free amino group by reacting the triaryl amine with a diazotation compound, to obtain a diazonium salt, to thereby obtain said biaryl compound comprising the diazonium salt and the triaryl amine.

11. The method of claim 9, wherein said position suitable for intramolecular cyclization is a 2,2' position.

12. The method of claim 10, wherein said arylating comprises reacting the diaminobiaryl compound with an aryl comprising a leaving group, optionally in the presence of a metal-based catalyst.

13. The method of claim 12, wherein said leaving group is selected from a halo group, a nitro group, an azo group, and a quaternary amino group.

14. The method of claim 12, wherein (i) a molar ratio of said diaminobiaryl compound to said metal-based catalyst is at least 1:0.01; and/or (ii) a molar ratio of said diaminobiaryl compound to said aryl comprising the leaving group is at least 1:1; and/or (iii) said diazotation compound comprises a source of nitroso compound (N≡O⁺); and/or (iv) said metal-based catalyst is a Cu(I) based catalyst; which further comprises a bidentate ligand.

15. The method of claim 10, wherein further comprising, prior to performing said intramolecular cyclization, mixing the diaminobiaryl compound or the biaryl compound with a solvent, thereby forming a solution, optionally wherein the diaminobiaryl compound is at a molar concentration ranging from 0.01 to 3 mol/L within said solution.

16. An article comprising the composition of claim 4.

17. The article of claim 16, being in a form of an alkaline fuel cell, an alkaline water electrolyzer, an alkaline redox-flow battery, a metal-air battery, or a capacitor.

18. The composition of claim 1, wherein said heteroaryl ring is selected from pyrrole, furane, thiophene, imidazole, oxazole, thiazole, pyrazole, pyridine, pyrimidine, quinoline, isoquinoline and purine.

* * * * *